US012807693B2

(12) United States Patent
Vikström et al.

(10) Patent No.: US 12,807,693 B2
(45) Date of Patent: Nov. 24, 2026

(54) METHOD OF PRODUCING A RECOMBINANT PROTEIN IN A HOST CELL WHICH HAS A DISABLED RHAMNOSE METABOLISM AS WELL AS EXPRESSION VECTORS, HOST CELLS AND RECOMBINANT PROTEINS THEREOF

(71) Applicants: STADA ARZNEIMITTEL AG, Bad Vilbel (DE); XBRANE BIOPHARMA AB, Stockholm (SE)

(72) Inventors: David Vikström, Upplands Väsby (SE); Nurzian Ismail, Stockholm (SE); Patrik Samuelson, Saltsjöbaden (SE); Kiavash Mirzadeh, Solna (SE); Santhosh Gudise, Farsta (SE); Maria Kadow, Sollentuna (SE); Kathleen Szekér, Marburg (DE); Tagrid Salih, Bromma Kyrka (SE); Mariusz Baraszkiewicz, Bromma (SE); Siavash Bashiri, Danderyd (SE)

(73) Assignees: STADA ARZNEIMITTEL AG, Bad Vilbel (DE); XBRANE BIOPHARMA AB, Stockholm (SE)

( * ) Notice: Subject to any disclaimer, the term of this patent is extended or adjusted under 35 U.S.C. 154(b) by 766 days.

(21) Appl. No.: 18/028,883

(22) PCT Filed: Oct. 8, 2021

(86) PCT No.: PCT/EP2021/077820

§ 371 (c)(1),
(2) Date: Mar. 28, 2023

(87) PCT Pub. No.: WO2022/074182

PCT Pub. Date: Apr. 14, 2022

(65) Prior Publication Data

US 2023/0340096 A1 Oct. 26, 2023

(30) Foreign Application Priority Data

Oct. 9, 2020 (EP) .................................... 20201096

(51) Int. Cl.
*C07K 16/22* (2006.01)
*C12N 15/70* (2006.01)

(52) U.S. Cl.
CPC .............. *C07K 16/22* (2013.01); *C12N 15/70* (2013.01); *C07K 2317/24* (2013.01); *C07K 2317/55* (2013.01)

(58) Field of Classification Search
CPC .............. C07K 16/241; C07K 2317/24; C07K 2317/55; C07K 2319/02; C07K 2317/14; C12N 15/70; C12N 15/1058; C12N 15/67; C12P 21/02; C40B 40/08
See application file for complete search history.

(56) References Cited

U.S. PATENT DOCUMENTS

| | | | | |
|---|---|---|---|---|
| 2005/0130205 | A1 | 6/2005 | Slater et al. | |
| 2006/0014291 | A1 * | 1/2006 | Kebeler | C12N 15/63 435/488 |
| 2013/0344099 | A1 | 12/2013 | Luirink et al. | |

FOREIGN PATENT DOCUMENTS

| | | | | |
|---|---|---|---|---|
| EP | 3260542 | A1 * | 12/2017 | C12N 15/8289 |
| JP | 2008522599 | A | 7/2008 | |
| JP | 2013236632 | A | 11/2013 | |
| JP | 2020520642 | A | 7/2020 | |
| WO | 2006061174 | | 6/2006 | |
| WO | 2012041899 | | 4/2012 | |
| WO | WO-2013142033 | A1 * | 9/2013 | C12N 9/001 |
| WO | WO-2016156465 | A1 * | 10/2016 | A61P 43/00 |
| WO | WO-2017077275 | A1 * | 5/2017 | A61P 37/04 |
| WO | WO-2018122794 | A1 * | 7/2018 | A61P 19/08 |
| WO | WO-2018211529 | A1 * | 11/2018 | C07K 16/22 |
| WO | WO-2020254876 | A1 * | 12/2020 | A61P 1/16 |

OTHER PUBLICATIONS

Hjelm et al., (2017) "Tailoring *Escherichia coli* for the I-Rhamnose PBAD Promoter-Based Production of Membrane and Secretory Proteins", ACS Synth. Biol., 6(6):985-994.
Kelly et al., (2019) "Transcriptional Terminators Allow Leak-Free Chromosomal Integration of Genetic Constructs in Cyanobacteria", Microorganisms, 7(263):1-9.
Kumar et al., (2019) "QbD Based Media Development for the Production of Fab Fragments in *E. coli*", Bioengineering, 6(29):1-17.
Sandomenico et al., (2020) "Evolution of *Escherichia coli* Expression System in Producing Antibody Recombinant Fragments", International Journal Of Molecular Sciences, 21(17):1-39.
Petrus et al., (2019) "A microbial expression system for high-level production of Scfv HIV-neutralizing antibody fragments in *Escherichia coli*", Applied Microbiology and Biotechnology, 103:8875-8888.
Orosz et al., (1991) "Analysis of the complex transcription termination region of the Escl,erichia coli rrnB gene", Eur. J. Biochem., 201:653-659.

(Continued)

*Primary Examiner* — Paul J Holland
(74) *Attorney, Agent, or Firm* — Kyle A. Gurley; Bozicevic, Field & Francis LLP

(57) ABSTRACT

The present invention relates to DNA construct suitable for expressing a recombinant protein in a bacterial host cell wherein said DNA construct comprises nucleotide sequences encoding: a rhaBAD promoter, a RhaR transcription activator, a RhaS transcription activator, an antibiotic resistance marker, a promoter operably linked to the nucleic acid encoding for the antibiotic resistance marker, an rrnB T1 terminator, an rrnB T2 terminator and a pMB1 origin of replication. The DNA construct may also comprise a nucleotide sequence encoding said recombinant protein operably linked to the rhaBAD promoter. The present invention further relates to a vector and bacterial host cell comprising said DNA construct as well as a method of producing said recombinant protein by exposing said bacterial host cell to rhamnose and thereby inducing expression of said recombinant protein.

28 Claims, 9 Drawing Sheets

Specification includes a Sequence Listing.

(56) References Cited

OTHER PUBLICATIONS

Corresponding Japanese Office Action JP2023-546386 dated Jun. 24, 2025, 68 pages.
Choi et al., (2004) "Secretory and extracellular production of recombinant proteins using *Escherichia coli*", Appl Microbiol Biotechnol, 64:625-635.
Giacalone et al., (2006) "Toxic protein expression in *Escherichia coli* using a rhamnose-based tightly regulated and tunable promoter system", BioTechniques, 40(3):355-364.
Holcroft & Egan, (2000) "Interdependence of Activation at rhaSR by Cyclic AMP Receptor Protein, the RNA Polymerase Alpha Subunit C-Terminal Domain, and RhaR", J. Bacteriol., 182(23):6774-6782.
Wilms et al., (2001) "High-Cell-Density Fermentation for Production of L-N-Carbamoylase Using an Expression System Based on the *Escherichia coli* rhaBAD Promoter", Biotechnology And Bioengineering, 73(2):95-103.
Corresponding Korean Office Action KR 2010-2023-7015497 dated Jun. 16, 2026, 10 pages.

* cited by examiner

METHOD OF PRODUCING A RECOMBINANT PROTEIN IN A HOST CELL WHICH HAS A DISABLED RHAMNOSE METABOLISM AS WELL AS EXPRESSION VECTORS, HOST CELLS AND RECOMBINANT PROTEINS THEREOF

TECHNICAL FIELD

The present invention relates to DNA construct suitable for expressing a recombinant protein in a bacterial host cell wherein said DNA construct comprises nucleotide sequences encoding: a rhaBAD promoter, a RhaR transcription activator, a RhaS transcription activator, an antibiotic resistance marker, at least one terminator, and an origin of replication. The DNA construct may also comprise a promoter operably linked to the nucleic acid encoding for the antibiotic resistance marker, and a nucleotide sequence encoding said recombinant protein operably linked to the rhaBAD promoter. The at least one terminator may be an rrnB T1 terminator and an rrnB T2 terminator. The recombinant protein may be ranibizumab. The present invention further relates to a vector and bacterial host cell comprising said DNA construct as well as a method of producing said recombinant protein by exposing said bacterial host cell to rhamnose and thereby inducing expression of said recombinant protein.

BACKGROUND OF THE INVENTION

The metabolism of rhamnose involves L-rhamnose being taken up into cells via the permease RhaT and then isomerized into L-rhamnulose by L-rhamnose isomerase (RhaA), and L-rhamnulose is then phosphorylated further by rhamnulokinase (RhaB) and finally hydrolyzed by rhamnulose-1-phosphate aldolase (RhaD) to give dihydroxyacetonephosphate and L-lactaldehyde [1]. The genes rhaA, rhaB and rhaD form an operon referred to as rhaBAD and are transcribed with the aid of the rhaBAD promoter [1]. In comparison with other systems, the rhamnose metabolism pathway is distinguished by the fact that two transcription activators known as RhaS and RhaR are required for regulation as explained below [1].

The rhaBAD operon is a positively regulated catabolic operon which transcribes above mentioned rhaB, rhaA and rhaD genes divergently from the rhaSR operon with approximately 240 bp of DNA separating their respective transcription start sites [1]. The rhaSR operon encodes RhaS and RhaR wherein each monomer of the dimeric RhaS and RhaR proteins contains two helix-turn-helix motifs and contacts two major grooves of DNA. RhaR regulates transcription of rhaSR by binding promoter DNA spanning −32 to −82 bases relative to the rhaSR transcription start site [1]. Subsequent to rhaSR expression, RhaS bind DNA upstream of the rhaBAD operon at −32 to −81 bases relative to the transcription start site to increase rhaBAD expression [1]. Furthermore, the rhaSR-rhaBAD intergenic region contains CRP binding sites at positions −92.5 (CRP 1) relative to the transcription start site of the rhaBAD operon and CRP binding sites at positions −92.5 (CRP 2), −115.5 (CRP 3) and −116.5 (CRP 4) relative to the transcription start site of the rhaSR operon [1]. The cyclic AMP receptor protein (CRP) regulates the expression of more than 100 promoters in *Escherichia coli.*

DNA constructs comprising DNA sequences encoding RhaS, RhaR and the rhaBAD promoter are known in the art. U.S. Pat. No. 8,138,324 discloses pTACO- and pLEMOderived plasmids (i.e. DNA constructs) comprising DNA sequences encoding RhaS, RhaR and the rhaBAD promoter. However, U.S. Pat. No. 8,138,324 is silent about using host cells which have a disabled rhamnose metabolism.

DNA constructs based on pRha-derived plasmids comprising DNA sequences encoding RhaS, RhaR and the rhaBAD promoter are also known in the art, for example from Giacalone et al. [5] or Hjelm et al. [2]. Giacalone et al. describe for example the plasmids pRha67A and pRha109A whereas Hjelm et al. disclose the plasmid pRha67K.

Although DNA constructs comprising DNA sequences encoding RhaS, RhaR and the rhaBAD promoter are known in the art there are still many challenges, especially in industrial scale production of recombinant proteins, in particular monoclonal antibodies or fragments thereof. The main challenges are:

(i) the host cells being subject to stress which results in damage to cellular macromolecules such as membranes, proteins and nucleic acids;
(ii) poor growth of the host cells;
(iii) poor activity of the produced recombinant proteins; and/or
(iv) obtaining recombinant proteins in low yields.

Accordingly, there is a need for improved DNA constructs as well as a host cell and method suitable for the efficient production of recombinant proteins, such as monoclonal antibodies or fragments thereof in a high yield, particularly when such recombinant proteins are intended for therapeutic applications.

OBJECTS OF THE INVENTION

Thus, the object of the present invention was to provide improved DNA constructs, as well as a bacterial host cell and method suitable for the efficient production of recombinant proteins, such as monoclonal antibodies or fragments thereof in a bacterial host cell in a high yield, particularly when such recombinant proteins are intended for therapeutic applications. The recombinant protein may be ranibizumab.

SUMMARY OF THE INVENTION

A first aspect of the invention relates to a DNA construct for expressing ranibizumab in a bacterial host cell, wherein ranibizumab comprises (i) a light chain comprising the amino acid sequence of SEQ ID 3, and (ii) a heavy chain comprising the amino acid sequence of SEQ ID 4, wherein said DNA construct comprises a nucleotide sequence encoding ranibizumab, wherein said DNA construct further comprises at least one nucleotide sequence encoding a signal peptide which is operably linked in the direction of transcription to the nucleotide sequence encoding the light chain of ranibizumab and/or the heavy chain of ranibizumab, wherein said DNA construct comprises nucleotide sequences encoding:

rhaBAD promoter,
RhaR transcription activator,
RhaS transcription activator,
an antibiotic resistance marker,
at least one terminator, and
an pMB1 origin of replication.

In a preferred embodiment, said DNA construct further comprises a nucleotide sequence encoding a promoter operably linked to the nucleotide sequence encoding the antibiotic resistance marker.

In a preferred embodiment, the DNA construct further comprises nucleotide sequences encoding rrnB T1 terminator and rrnB T2 terminator.

In a preferred embodiment, the DNA construct is characterized by:

- the antibiotic resistance marker is a kanamycin resistance marker, preferably a kanamycin resistance marker comprising the nucleotide sequence of SEQ ID 12 or a sequence with at least 90% sequence identity thereto;
- the promoter operably linked to the nucleotide sequence encoding the antibiotic resistance marker is an AmpR promoter, preferably an AmpR promoter comprising the nucleotide sequence of SEQ ID 13 or a sequence with at least 90% sequence identity thereto;
- the rrnB T1 terminator comprising the nucleotide sequence of SEQ ID 14 or a sequence with at least 90% sequence identity thereto;
- the rrnB T2 terminator comprising the nucleotide sequence of SEQ ID 15 or a sequence with at least 90% sequence identity thereto; and/or
- the pMB1 origin of replication comprising the nucleotide sequence of SEQ ID 16 or a sequence with at least 90% sequence identity thereto.

In a preferred embodiment, the DNA construct is characterized by:

- the antibiotic resistance marker being a kanamycin resistance marker comprising the nucleotide sequence of SEQ ID 12;
- the promoter operably linked to the nucleotide sequence encoding the antibiotic resistance marker is an AmpR promoter comprising the nucleotide sequence of SEQ ID 13;
- the rrnB T1 terminator comprising the nucleotide sequence of SEQ ID 14;
- the rrnB T2 terminator comprising the nucleotide sequence of SEQ ID 15; and/or
- the pMB1 origin of replication comprising the nucleotide sequence of SEQ ID 16.

In a preferred embodiment, the DNA construct is characterized by:

- the rhaBAD promoter comprising the nucleotide sequence of SEQ ID 8 or a sequence with at least 90% sequence identity thereto;
- the RhaR transcription activator comprising the nucleotide sequence of SEQ ID 9 or a sequence with at least 90% sequence identity thereto;
- the RhaS transcription activator comprising the nucleotide sequence of SEQ ID 11 or a sequence with at least 90% sequence identity thereto;
- the antibiotic resistance marker is a kanamycin resistance marker comprising the nucleotide sequence of SEQ ID 12 or a sequence with at least 90% sequence identity thereto;
- the AmpR promoter comprising the nucleotide sequence of SEQ ID 13 or a sequence with at least 90% sequence identity thereto;
- the rrnB T1 terminator comprising the nucleotide sequence of SEQ ID 14 or a sequence with at least 90% sequence identity thereto;
- the rrnB T2 terminator comprising the nucleotide sequence of SEQ ID 15 or a sequence with at least 90% sequence identity thereto; and
- the pMB1 origin of replication comprising the nucleotide sequence of SEQ ID 16 or a sequence with at least 90% sequence identity thereto.

In a preferred embodiment, the DNA construct is characterized by:

- the rhaBAD promoter comprising the nucleotide sequence of SEQ ID 8;
- the RhaR transcription activator comprising the nucleotide sequence of SEQ ID 9;
- the RhaS transcription activator comprising the nucleotide sequence of SEQ ID 11;
- the antibiotic resistance marker is a kanamycin resistance marker comprising the nucleotide sequence of SEQ ID 12;
- the AmpR promoter comprising the nucleotide sequence of SEQ ID 13;
- the rrnB T1 terminator comprising the nucleotide sequence of SEQ ID 14;
- the rrnB T2 terminator comprising the nucleotide sequence of SEQ ID 15; and
- the pMB1 origin of replication comprising the nucleotide sequence of SEQ ID 16.

In a preferred embodiment, the DNA construct comprises a multiple cloning site comprising 17 restriction sites cleavable by restriction enzymes EcoRI, NdeI, NotI, XhoI, PspXI, PaeR71, BbsI, StyI, AvrII, BanI, Acc65I, KpnI, Eco53kI, SacI, BamHI, XbaI, SalI, AccI, PstI, SbfI, SphI and HindIII.

In a preferred embodiment, the DNA construct comprises the nucleotide sequence of SEQ ID 1, or a sequence with at least 90% sequence identity thereto, preferably the nucleotide sequence of SEQ ID 1.

In a preferred embodiment, the nucleotide sequence encoding ranibizumab is operably linked to the rhaBAD promoter.

In a preferred embodiment, the nucleotide sequence encoding ranibizumab comprises (i) a nucleotide sequence encoding for the light chain of ranibizumab comprising the sequence of SEQ ID 5 or a sequence with at least 90% sequence identity thereto, and/or (ii) a nucleotide sequence encoding for the heavy chain of ranibizumab comprising the sequence of SEQ ID 6 or a sequence with at least 90% sequence identity thereto. In a further preferred embodiment, said nucleotide sequence encoding ranibizumab comprises (i) a nucleotide sequence encoding for the light chain of ranibizumab comprising the sequence of SEQ ID 5, and/or (ii) a nucleotide sequence encoding for the heavy chain of ranibizumab comprising the sequence of SEQ ID 6.

In an embodiment, the nucleotide sequence encoding the signal peptide is operably linked in the direction of transcription to either one or both of the nucleotide sequence of SEQ ID 5 and SEQ ID 6.

In an embodiment, the signal peptide is PelB (pectate lyase B). In a preferred embodiment, the nucleotide sequence encoding the PelB signal peptide comprises a sequence of SEQ ID 7 or a sequence with at least 90% sequence identity thereto; more preferably the nucleotide sequence encoding the PelB signal peptide comprises the sequence of SEQ ID 7.

In one embodiment, the resulting PelB signal peptide comprises an amino acid sequence of SEQ ID 18 [6]: MKYLLPTAAAGLLLLAAQPAMA.

In a preferred embodiment, the DNA construct comprises the sequence of SEQ ID 17 or a sequence with at least 90% sequence identity thereto, preferably comprises the sequence of SEQ ID 17.

A second aspect of the invention relates to an expression vector comprising any of the DNA constructs according to the first aspect of the invention.

A third aspect of the invention relates to a bacterial host cell comprising a DNA construct according to the first aspect of the invention or the expression vector according to the second aspect of the invention, wherein said bacterial host cell is preferably an *Escherichia coli* cell, more preferably an *E. coli* K-12 cell.

In a preferred embodiment, said bacterial host cell either comprises (i) a chromosome which comprises a mutation in the nucleic acid sequence of the rhaB gene which renders RhaB inactive, or (ii) a chromosome in which the nucleotide sequence encoding RhaB is deleted.

In a preferred embodiment, said bacterial host cell is an *Escherichia coli* W3110 cell, preferably comprising a chromosome which comprises a frame shift-mutation in the nucleotide sequence encoding RhaB.

In a preferred embodiment, said bacterial host cell is an *Escherichia coli* W3110 cell comprising a chromosome which comprises nucleotide sequence of SEQ ID 2 or a sequence with at least 90% sequence identity thereto, preferably the nucleotide sequence of SEQ ID 2, wherein optionally the chromosome of the bacterial host cell further comprises a nucleotide sequence encoding RhaT.

A fourth aspect of the invention relates to a method of producing ranibizumab comprising the step of exposing the bacterial host cell according to the third aspect of the invention to rhamnose, thereby inducing expression of ranibizumab. In a preferred embodiment, the method further comprises the step of recovering ranibizumab from the bacterial host cell; and optionally further comprises one or more step(s) of purifying the recovered ranibizumab, preferably by one or more chromatography steps.

A fifth aspect of the invention relates to a method of producing ranibizumab, comprising the steps of:

cloning nucleotide sequence encoding a recombinant protein into a DNA construct which comprises a nucleotide sequence of SEQ ID 1 or a sequence with at least 90% sequence identity thereto, preferably a nucleotide sequence of SEQ ID 1, such that the nucleotide sequence encoding ranibizumab protein is operably linked to the rhaBAD promoter; and a. introducing the resulting nucleotide sequence into a bacterial host cell comprising a chromosome which comprises a mutation or modification which disables rhamnose metabolism.

In a preferred embodiment, the method further comprises the step of exposing the bacterial host cell to rhamnose, thereby inducing expression of the recombinant protein.

In another embodiment, the method further comprises the step of recovering ranibizumab from the bacterial host cell; and optionally further comprises one or more step(s) of purifying the recovered ranibizumab, preferably by one or more chromatography steps.

In a preferred embodiment, said bacterial host cell is an *Escherichia coli* cell, more preferably an *E. coli* K-12 cell, most preferably an *E. coli* W3110 cell.

In a preferred embodiment, said bacterial host cell either comprises (i) a chromosome which comprises a mutation in the nucleotide sequence of the rhaB gene which renders RhaB inactive, or (ii) a chromosome in which the nucleotide sequence encoding RhaB is deleted.

In a preferred embodiment, said bacterial host cell is an *E. coli* W3110 cell comprising a chromosome which comprises a frame shift-mutation in the nucleotide sequence encoding RhaB.

In a preferred embodiment, said bacterial host cell is an *E. coli* W3110 cell comprising a chromosome which comprises the nucleotide sequence of SEQ ID 2 or a sequence with at least 90% sequence identity thereto, preferably the nucleotide sequence of SEQ ID 2, wherein optionally the chromosome of the bacterial host cell further comprises a nucleotide sequence encoding RhaT.

In a preferred embodiment, said nucleotide sequence encoding ranibizumab comprises (i) a nucleotide sequence encoding the light chain of ranibizumab comprising the sequence of SEQ ID 5 or a sequence with at least 90% sequence identity thereto, and/or (ii) a nucleotide sequence encoding for the heavy chain of ranibizumab comprising the sequence of SEQ ID 6 or a sequence with at least 90% sequence identity thereto; preferably said nucleotide sequence encoding the recombinant protein comprises (i) a nucleotide sequence encoding for the light chain of ranibizumab comprising the sequence of SEQ ID 5, and/or (ii) a nucleotide sequence encoding for the heavy chain of ranibizumab comprising the sequence of SEQ ID 6.

In a preferred embodiment, a nucleotide sequence comprising SEQ ID 5 and/or SEQ ID 6 further comprises a nucleotide sequence encoding a signal peptide which is operably linked in the direction of transcription to the nucleotide sequence of SEQ ID 5 and/or SEQ ID 6.

In a preferred embodiment, said nucleotide sequence encoding the signal peptide is a nucleotide sequence encoding a PelB signal peptide, preferably the nucleotide sequence encoding the PelB signal peptide comprises the sequence of SEQ ID 7 or a sequence with at least 90% sequence identity thereto; preferably the nucleotide sequence encoding the PelB signal peptide comprises the sequence of SEQ ID 7 and is fused to the nucleotide sequence encoding the light chain and/or heavy chain of ranibizumab.

In a preferred embodiment, the resulting nucleotide sequence to be introduced into the bacterial host cell comprises the sequence of SEQ ID 17 or a sequence with at least 90% sequence identity thereto, preferably comprises the sequence of SEQ ID 17.

A sixth aspect of the invention relates to a bacterial host cell being an *E. coli* W3110 cell and comprising a chromosome which comprises a frame shift-mutation in the nucleotide sequence encoding RhaB. In an embodiment, said *E. coli* W3110 host cell comprises a chromosome which comprises the nucleotide sequence of SEQ ID 2 or a sequence with at least 90% sequence identity thereto, preferably the nucleotide sequence of SEQ ID 2. In a further embodiment the chromosome of the bacterial host cell comprises a nucleotide sequence encoding RhaT.

One or more of the above indicated SEQ IDs 1-18 of the various aspects of the invention (and embodiments thereof) may be replaced by a sequence with at least 90% sequence identity thereto. The term "sequence identity" as used herein is used with regard to amino acid or nucleotide sequences and the sequence identity is over the entire length of the specified sequence. A sequence may thus be at least 90 percent, at least 92 percent, at least 95 percent, at least 96 percent, at least 97 percent, at least 98 percent or at least 99 percent, identical in sequence to the amino acid or nucleotide sequence specified. Such sequences of the invention thus include single or multiple nucleotide or amino acid alterations (additions, substitutions, insertions or deletions) to the sequences of the invention. At the amino acid level preferred sequences with the above defined sequence identity contain up to 5, e.g. only 1, 2, 3, 4 or 5, preferably 1, 2 or 3, more preferably 1 or 2, altered amino acids in the sequences of the invention.

DETAILED DESCRIPTION

The present invention relates to regulating the L-rhamnose rhaBAD promoter-based production of recombinant proteins.

More specifically, the present invention relates to producing a recombinant protein, preferably ranibizumab, comprising the steps of:

a. cloning an a nucleotide sequence encoding a recombinant protein, preferably ranibizumab, into a DNA construct such that the nucleotide sequence is operably linked to a rhaBAD promoter, and b. introducing the resulting nucleotide sequence into a bacterial host cell comprising a chromosome which comprises a mutation or modification which disables rhamnose metabolism.

Figure 1:
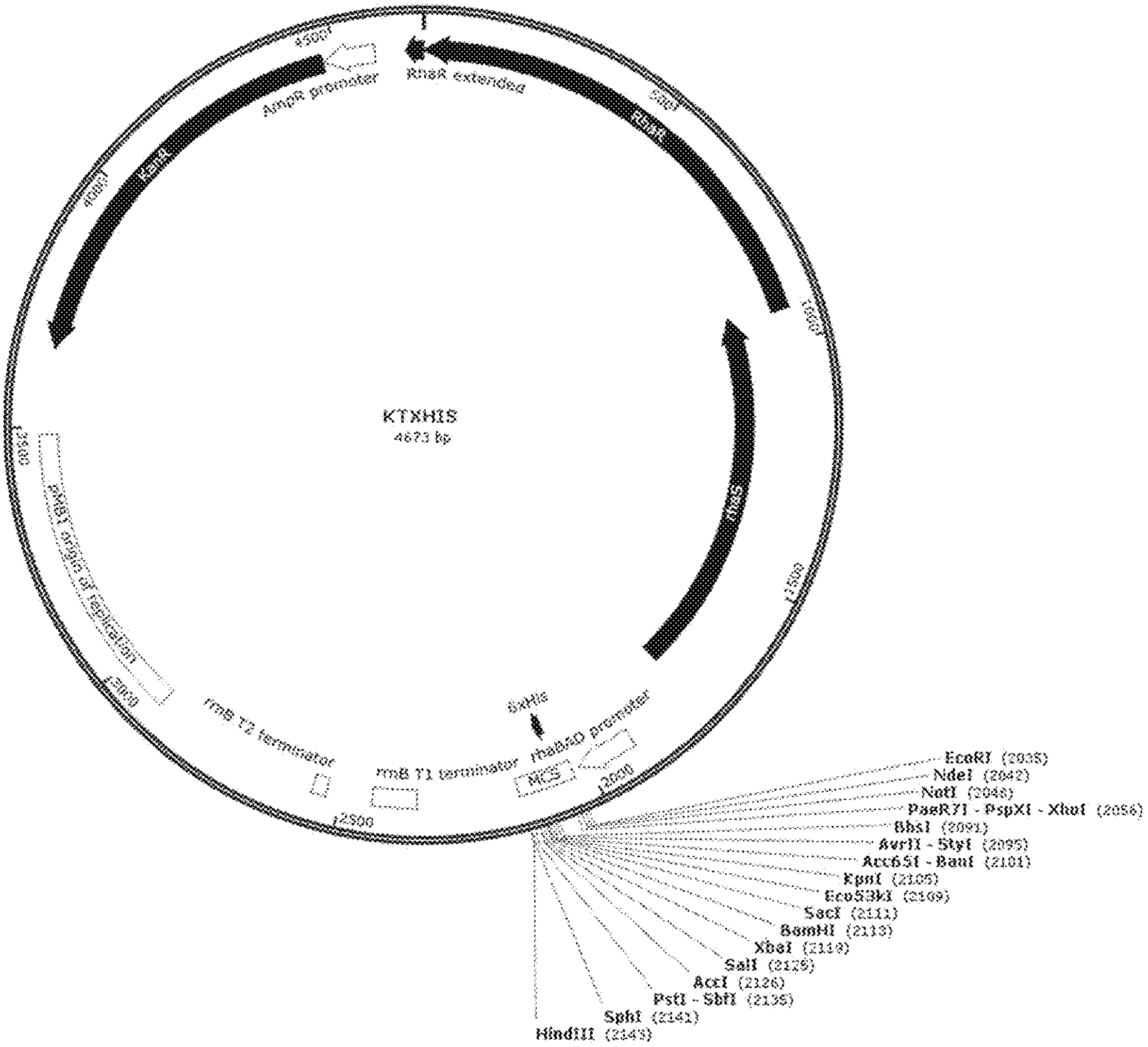
FIG. 1—Plasmid map for KTXHIS

The DNA construct disclosed in the above method may comprise a nucleotide sequence encoding the rhaBAD promoter. In an embodiment of the invention, the nucleotide sequence of the rhaBAD promoter comprises the sequence of SEQ ID 8 (and wherein the sequence is referred to as "rhaBAD" in FIGS. 1 and 3):

```
CACCACAATTCAGCAAATTGTGAACATCATCACGTTCATCTTTCCCTGGT
TGCCAATGGCCCATTTTCTTGTCAGTAACGAGAAGGTCGCGAATCCAGGC
GCTTTTTAGACTGGTCGTA.
```

The DNA construct may comprise a nucleotide sequence encoding the RhaR transcription activator. In an embodiment of the invention, the nucleotide sequence of the RhaR transcription activator comprises a sequence of SEQ ID 9 (and wherein the sequence is referred to as "rhaR" in FIGS. 1 and 3):

```
ATGGCTTTCTGCAATAACGCGAATCTTCTCAACGTATTTGTACGCCATAT
TGCGAATAATCAACTTCGTTCTCTGGCCGAGGTAGCCACGGTGGCGCATC
AGTTAAAACTTCTCAAAGATGATTTTTTTGCCAGCGACCAGCAGGCAGTC
GCTGTGGCTGACCGTTATCCGCAAGATGTCTTTGCTGAACATACACATGA
TTTTTGTGAGCTGGTGATTGTCTGGCGCGGTAATGGCCTGCATGTACTCA
ACGATCGCCCTTATCGCATTACCCGTGGCGATCTCTTTTACATTCATGCT
GATGATAAACACTCCTACGCTTCCGTTAACGATCTGGTTTTGCAGAATAT
```

-continued

```
TATTTATTGCCCGGAGCGTCTGAAGCTGAATCTTGACTGGCAGGGGGCGA
TTCCGGGATTTAACGCCAGCGCAGGGCAACCACACTGGCGCTTAGGTAGC
ATGGGGATGGCGCAGGCGCGGCAGGTTATTGGTCAGCTTGAGCATGAAAG
TAGTCAGCATGTGCCGTTTGCTAACGAAATGGCTGAGTTGCTGTTCGGGC
AGTTGGTGATGTTGCTGAATCGCCATCGTTACACCAGTGATTCGTTGCCG
CCAACATCCAGCGAAACGTTGCTGGATAAGCTGATTACCCGGCTGGCGGC
TAGCCTGAAAAGTCCCTTTGCGCTGGATAAATTTTGTGATGAGGCATCGT
GCAGTGAGCGCGTTTTGCGTCAGCAATTTCGCCAGCAGACTGGAATGACC
ATCAATCAATATCTGCGACAGGTCAGAGTGTGTCATGCGCAATATCTTCT
CCAGCATAGCCGCCTGTTAATCAGTGATATTTCGACCGAATGTGGCTTTG
AAGATAGTAACTATTTTTCGGTGGTGTTTACCCGGGAAACCGGGATGACG
CCCAGCCAGTGGCGTCATCTCAATTCGCAGAAAGAT.
```

The DNA construct may further comprise a nucleotide sequence encoding an extension of the RhaR transcription activator which is in frame with RhaR because of a missing stop codon. In an embodiment of the invention, the nucleotide sequence of the extension of the RhaR transcription activator comprises the sequence of SEQ ID 10 (and wherein the sequence is referred to as "rhaR extended" in FIGS. 1 and 3):

```
AGACGAAAGGGCCTCGTGATACGCCTATTTTTATAG.
```

The DNA construct may comprise a nucleotide sequence encoding the RhaS transcription activator. In an embodiment of the invention, the nucleotide sequence of the RhaS transcription activator comprises the sequence of SEQ ID 11 (and wherein the sequence is referred to as "rhaS" in FIGS. 1 and 3):

```
ATGACCGTATTACATAGTGTGGATTTTTTTCCGTCTGGTAACGCGTCCGT
GGCGATAGAACCCCGGCTCCCGCAGGCGGATTTTCCTGAACATCATCATG
ATTTTCATGAAATTGTGATTGTCGAACATGGCACGGGTATTCATGTGTTT
AATGGGCAGCCCTATACCATCACCGGTGGCACGGTCTGTTTCGTACGCGA
TCATGATCGGCATCTGTATGAACATACCGATAATCTGTGTCTGACCAATG
TGCTGTATCGCTCGCCGGATCGATTTCAGTTTCTCGCCGGGCTGAATCAG
TTGCTGCCACAAGAGCTGGATGGGCAGTATCCGTCTCACTGGCGCGTTAA
CCACAGCGTATTGCAGCAGGTGCGACAGCTGGTTGCACAGATGGAACAGC
AGGAAGGGGAAAATGATTTACCCTCGACCGCCAGTCGCGAGATCTTGTTT
ATGCAATTACTGCTCTTGCTGCGTAAAAGCAGTTTGCAGGAGAACCTGGA
AAACAGCGCATCACGTCTCAACTTGCTTCTGGCCTGGCTGGAGGACCATT
TTGCCGATGAGGTGAATTGGGATGCCGTGGCGGATCAATTTTCTCTTTCA
CTGCGTACGCTACATCGGCAGCTTAAGCAGCAAACGGGACTGACGCCTCA
GCGATACCTGAACCGCCTGCGACTGATGAAAGCCCGACATCTGCTACGCC
ACAGCGAGGCCAGCGTTACTGACATCGCCTATCGCTGTGGATTCAGCGAC
AGTAACCACTTTTCGACGCTTTTTCGCCGAGAGTTTAACTGGTCACCGCG
TGATATTCGCCAGGGACGGGATGGCTTTCTGCAATAA.
```

The DNA construct may comprise a nucleotide sequence encoding an "antibiotic resistance marker" or "selection marker". Such a marker is a fragment of DNA that contains a gene whose product confers resistance to an antibiotic (e.g., chloramphenicol, ampicillin, gentamycin, streptomycin, tetracycline, kanamycin, neomycin) or the ability to grow on selective media (e.g., ura (uracil), leu (leucine), trp (tryptophan), his (histidine)). Usually, plasmids contain antibiotic resistance marker to force the bacterial cell to maintain the plasmid. In an embodiment of the invention, the DNA construct may comprise a nucleotide sequence of a kanamycin resistance marker. In a specific embodiment of the invention, the nucleotide sequence for conferring kanamycin resistance comprises the sequence of SEQ ID 12 (and wherein the sequence is referred to as "KanR" in FIGS. 1 and 3):

```
ATGAGCCATATTCAACGGGAAACGTCTTGCTCTAGGCCGCGATTAAATTC
CAACATGGATGCTGATTTATATGGGTATAAATGGGCTCGCGATAATGTCG
GGCAATCAGGTGCGACAATCTATCGATTGTATGGGAAGCCCGATGCGCCA
GAGTTGTTTCTGAAACATGGCAAAGGTAGCGTTGCCAATGATGTTACAGA
TGAGATGGTCAGACTAAACTGGCTGACGGAATTTATGCCTCTTCCGACCA
TCAAGCATTTTATCCGTACTCCTGATGATGCATGGTTACTCACCACTGCG
ATCCCCGGGAAAACAGCATTCCAGGTATTAGAAGAATATCCTGATTCAGG
TGAAAATATTGTTGATGCGCTGGCAGTGTTCCTGCGCCGGTTGCATTCGA
TTCCTGTTTGTAATTGTCCTTTTAACAGCGATCGCGTATTTCGTCTCGCT
CAGGCGCAATCACGAATGAATAACGGTTTGGTTGATGCGAGTGATTTTGA
TGACGAGCGTAATGGCTGGCCTGTTGAACAAGTCTGGAAAGAAATGCATA
AACTTTTGCCATTCTCACCGGATTCAGTCGTCACTCATGGTGATTTCTCA
CTTGATAACCTTATTTTTGACGAGGGGAAATTAATAGGTTGTATTGATGT
TGGACGAGTCGGAATCGCAGACCGATACCAGGATCTTGCCATCCTATGGA
ACTGCCTCGGTGAGTTTTCTCCTTCATTACAGAAACGGCTTTTTCAAAAA
TATGGTATTGATAATCCTGATATGAATAAATTGCAGTTTCATTTGATGCT
CGATGAGTTTTTCTAA.
```

The DNA construct may comprise a nucleotide sequence encoding a promoter operably linked to the nucleic acid sequence encoding the antibiotic resistance marker. Such a promotor may increase the expression of the antibiotic resistance markers discussed in the previous paragraph. In an embodiment of the invention, the promoter for ampicillin resistance is an AmpR promoter which is not only capable of promoting expression of ampicillin resistance markers but also capable of promoting expression of kanamycin resistance markers. In a specific embodiment of the invention, the nucleic acid sequence of the AmpR promoter comprises the sequence of SEQ ID 13 (and wherein the sequence is referred to as "AmpR promoter" in FIGS. 1 and 3):

```
CGCGGAACCCCTATTTGTTTATTTTTCTAAATACATTCAAATATGTATCC
GCTCATGAGACAATAACCCTGATAAATGCTTCAATAATATTGAAAAAGGA
AGAGT
```

The DNA construct may comprise a nucleotide sequence encoding for at least one terminator. The DNA construct may comprise a nucleotide sequence encoding for both of the rrnB T1 terminator and the rrnB T2 terminator. The rrnB T1 and T2 terminators are both efficient transcription terminators in isolated forms, however, when used together, rrnB T1 and T2 terminators may more efficiently terminate transcription.

In a specific embodiment of the invention, the nucleotide sequence of the rrnB T1 terminator comprises the sequence of SEQ ID 14:

```
CAAATAAAACGAAAGGCTCAGTCGAAAGACTGGGCCTTTCGTTTTATCTG
TTGTTTGTCGGTGAACGCTCTCCTGAGTAGGACAAAT
```

In a specific embodiment of the invention, the nucleotide sequence of the rrnB T2 terminator comprises the sequence of SEQ ID 15:

```
AGAAGGCCATCCTGACGGATGGCCTTTT
```

The DNA construct may further comprise an origin of replication which is a particular nucleotide sequence at which DNA replication is initiated. DNA replication may proceed from this point bidirectionally or unidirectionally. Some commonly used origins of replication are ColE1, pMB1, pSC101, R6K, pBR322, R6K, p15A, and pUC. In an embodiment of the invention, the origin of replication is pMB1 or derivatives thereof. In a specific embodiment of the invention, the nucleic acid sequence of pMB1 comprises the sequence of SEQ ID 16:

```
TTTCCATAGGCTCCGCCCCCCTGACGAGCATCACAAAAATCGACGCTCAA
GTCAGAGGTGGCGAAACCCGACAGGACTATAAAGATACCAGGCGTTTCCC
CCTGGAAGCTCCCTCGTGCGCTCTCCTGTTCCGACCCTGCCGCTTACCGG
ATACCTGTCCGCCTTTCTCCCTTCGGGAAGCGTGGCGCTTTCTCATAGCT
CACGCTGTAGGTATCTCAGTTCGGTGTAGGTCGTTCGCTCCAAGCTGGGC
TGTGTGCACGAACCCCCCGTTCAGCCCGACCGCTGCGCCTTATCCGGTAA
CTATCGTCTTGAGTCCAACCCGGTAAGACACGACTTATCGCCACTGGCAG
CAGCCACTGGTAACAGGATTAGCAGAGCGAGGTATGTAGGCGGTGCTACA
GAGTTCTTGAAGTGGTGGCCTAACTACGGCTACACTAGAAGGACAGTATT
TGGTATCTGCGCTCTGCTGAAGCCAGTTACCTTCGGAAAAAGAGTTGGTA
GCTCTTGATCCGGCAAACAAACCACCGCTGGTAGCGGTGGTTTTTTTGTT
TGCAAGCAGCAGATTACGCGCAGAAAAAAAGGATCTCAA
```

In an alternative embodiment of the invention, the DNA construct is an expression plasmid which comprises a nucleotide sequence encoding one or more of:

rhaBAD promoter,
RhaR transcription activator,
RhaS transcription activator,
an antibiotic resistance marker,
at least one terminator, and
an origin of replication,
wherein the DNA construct optionally comprises a multiple cloning site comprising 17 restriction sites cleavable by restriction enzymes EcoRI, NdeI, NotI, XhoI, PspXI, PaeR71, BbsI, StyI, AvrII, BanI, Acc65I, KpnI, Eco53kI, SacI, BamHI, XbaI, SalII, AccI, PstI, SbfI, SphI and HindIII. Optionally, the DNA construct further comprises a nucleotide sequence encoding a promoter operably linked to the nucleotide sequence encoding the antibiotic resistance marker and/or nucleotide sequences encoding rrnB T1 terminator and rrnB T2 terminator.

In an embodiment of the invention, the above disclosed expression plasmid comprises a nucleotide sequence encoding:

rhaBAD promoter,
RhaR transcription activator,
RhaS transcription activator,
an antibiotic resistance marker,
at least one terminator, and
an origin of replication.

Optionally, the DNA construct further comprises a nucleotide sequence encoding a promoter operably linked to the nucleotide sequence encoding the antibiotic resistance marker and/or nucleotide sequences encoding rrnB T1 terminator and rrnB T2 terminator.

In an embodiment of the invention, the above disclosed expression plasmid comprises a nucleotide sequence encoding:

rhaBAD promoter,
RhaR transcription activator,
RhaS transcription activator,
a kanamycin resistance marker,
AmpR promoter,
at least one terminator, and
pMB1 origin of replication.

Optionally, the nucleotide sequence encoding AmpR promoter is operably linked to the nucleotide sequence encoding the kanamycin resistance marker and/or the DNA construct further comprises nucleotide sequences encoding rrnB T1 terminator and rrnB T2 terminator.

In an embodiment of the invention, the above disclosed expression plasmid comprises nucleotide sequences encoding:

rhaBAD promoter comprising the nucleotide sequence of SEQ ID 8,
RhaR transcription activator comprising the nucleotide sequence of SEQ ID 9,
RhaS transcription activator comprising the nucleotide sequence of SEQ ID 11,
a kanamycin resistance marker comprising the nucleotide sequence of SEQ ID 12,
AmpR promoter comprising the nucleotide sequence of SEQ ID 13,
rrnB T1 terminator comprising the nucleotide sequence of SEQ ID 14,
rrnB T2 terminator comprising the nucleotide sequence of SEQ ID 15, and
pMB1 origin of replication comprising the nucleotide sequence of SEQ ID 16.

In an embodiment of the invention, the DNA construct is a plasmid which comprises the nucleotide sequence of SEQ ID 1 and wherein said DNA construct is also referred to as KTXHIS in the present invention.

The nucleotide sequence encoding a recombinant protein which is to be cloned into the DNA constructs described above may comprise a nucleic acid encoding a monoclonal antibody or fragment thereof, preferably ranibizumab or a fragment thereof. In a specific embodiment of the invention, the nucleic acid encoding ranibizumab comprises a nucleic acid encoding the heavy and light chains of ranibizumab. Ranibizumab is a monoclonal antibody fragment (Fab) which is an anti-angiogenic that has been approved to treat the "wet" type of age-related macular degeneration, a common form of age-related vision loss.

In a specific embodiment of the invention, the nucleotide sequence encoding the heavy chain of ranibizumab comprises the sequence of SEQ ID 6:

```
GAAGTTCAGCTGGTTGAAAGCGGTGGTGGTCTGGTTCAGCCTGGTGGTAG
CCTGCGTCTGAGCTGTGCAGCAAGCGGTTATGATTTTACCCATTATGGTA
TGAATTGGGTTCGTCAGGCACCGGGTAAAGGTCTGGAATGGGTTGGTTGG
ATTAATACCTATACCGGTGAACCGACCTATGCAGCAGATTTTAAACGTCG
TTTTACCTTTAGCCTGGATACCAGCAAAAGCACCGCATATCTGCAGATGA
ATAGCCTGCGTGCAGAGGATACCGCAGTGTATTATTGTGCAAAATATCCG
TATTATTACGGCACCAGCCATTGGTATTTCGATGTTTGGGGTCAGGGCAC
CCTGGTTACCGTTAGCAGCGCAAGCACCAAAGGTCCGAGCGTTTTTCCGC
TGGCACCGAGCAGCAAAAGTACCAGCGGTGGCACCGCAGCACTGGGTTGT
CTGGTTAAAGATTATTTTCCGGAACCGGTTACCGTGAGCTGGAATAGCGG
TGCACTGACCAGCGGTGTTCATACCTTTCCGGCAGTTCTGCAGAGCAGCG
GTCTGTATAGCCTGAGCAGCGTTGTTACCGTTCCGAGCAGCAGCCTGGGC
ACCCAGACCTATATTTGTAATGTTAATCATAAACCGAGCAATACCAAAGT
GGATAAAAAAGTGGAACCGAAAAGCTGCGATAAAACCCATCTGTAA.
```

In a specific embodiment of the invention, the nucleotide sequence encoding the light chain of ranibizumab comprises the sequence of SEQ ID 5:

```
GATATTCAGCTGACCCAGAGCCCGAGCAGCCTGAGCGCAAGCGTTGGTGA
TCGTGTTACCATTACCTGTAGCGCAAGCCAGGATATTAGCAATTATCTGA
ATTGGTATCAGCAGAAACCGGGTAAAGCACCGAAAGTGCTGATCTATTTT
ACCAGCAGCCTGCATAGCGGTGTTCCGAGCCGTTTTAGCGGTAGCGGTAG
TGGCACCGATTTTACCCTGACCATTAGCAGCCTGCAGCCGGAAGATTTTG
CAACCTATTATTGTCAGCAGTATAGCACCGTTCCGTGGACCTTTGGTCAG
GGCACCAAAGTTGAAATTAAACGTACCGTTGCAGCACCGAGCGTTTTTAT
CTTTCCGCCTAGTGATGAACAGCTGAAAAGCGGCACCGCAAGCGTTGTTT
GTCTGCTGAATAACTTTTATCCGCGTGAAGCAAAAGTTCAGTGGAAAGTT
GATAATGCACTGCAGAGCGGTAATAGCCAAGAAAGCGTTACCGAACAGGA
TAGCAAAGATAGCACCTATAGCCTGAGCAGCACCCTGACCCTGAGCAAAG
CAGATTATGAAAAACACAAAGTGTATGCCTGCGAAGTTACCCATCAGGGT
CTGAGCAGTCCGGTTACCAAAAGTTTTAATCGTGGTGAATGCTAA.
```

In a further embodiment of the invention, the nucleic acid encoding the heavy and light chains of ranibizumab further comprises a nucleotide sequence encoding a signal peptide operably linked to either one or both of the nucleotide sequences encoding the heavy and light chains of ranibizumab. The nucleic acid sequence encoding the signal peptide may be a nucleotide sequence encoding the PelB signal peptide. In a specific embodiment of the invention, the nucleotide sequence encoding the PelB signal peptide comprises the sequence of SEQ ID 7:

ATGAAATATCTGCTGCCGACCGCAGCAGCGGGTCTGCTGCTGCTGGCAGC

ACAGCCTGCAATGGCA.

The resulting nucleotide sequence (i.e. the product of cloning an nucleotide sequence encoding a recombinant protein, preferably ranibizumab, into a DNA construct) is preferably the nucleotide sequence of SEQ ID 17 which is also referred to as KTXHIS-PelbLC-PelbHC in the present invention.

The bacterial host cell to be used for producing the recombinant protein comprises a chromosome having a mutation or modification which disables rhamnose metabolism. The bacterial host cell may be an *E. coli* cell. In a preferred embodiment, the bacterial host cell is an *E. coli* K-12 cell, more preferably the bacterial host cell is an *E. coli* W3110 cell. The disabled rhamnose metabolism is achieved by a mutation in the nucleotide sequence encoding RhaB which renders RhaB inactive. Alternatively, the disabled rhamnose metabolism is achieved by using a bacterial host cell having a chromosome in which the nucleotide sequence encoding RhaB is deleted; this can e.g. be achieved by deleting the nucleotide sequence encoding RhaB. Preferably, the chromosome of the bacterial host cell comprises the nucleic acid sequence encoding RhaT, i.e. the RhaT gene is intact.

In an embodiment of the invention, the disabled rhamnose metabolism is achieved by a frame shift-mutation in the nucleotide sequence encoding RhaB. Such a mutation results in a bacterial host cell having a chromosome which comprises the nucleotide sequence of SEQ ID 2:

GTTGGCCCCGCTCCACGCCAGTAGCGACTCGTCCCAGTCGTCGCTATTGA

TATTGACCAGTTGCGTGGTCGTGGCGTTGGTATATTCCCAGTTCATCTTG

CCGGTCAGGCGATAACTGAAGTAATCCGGCATCAGCAGAGCGTGAGCAAT

GTGTGGAATAAGTTCAGGTTGTTGCTCCGTCAGCGCACGCAACTGATAAA

GCGTATTGAAGGGCAGAAACTGGATGCCGCTACGTTGATAAATATCGCGT

TTGCCGAGTTGTTGTTGTGCCTGCGCCATTAGGCCATTGGTGCGGCTATC

GCGATAAGCAACGGGCAGGCCCACACGCTGACCCTGTTGGTCGAGCAGCA

CAAAGTCCACGCCCCAGGTATCAATCCCAATGCTATCGCGATACGAATCC

CTTCCTCGCACACCTTGTTTAATCCAAGGCGAATGGCACTTTCCAGGCTA

TCCACATCCCAGGTGACATAGCCGTTCTGACTATGCAGCCCATTGTTAAA

ACGATGGATTTCGCGCAGCGTCAGGCTGCGGCATTCACGCTCGTAACGCG

CCAGCATCACGCGCCCACTGGATGCGCCGAGATCGACGGCGACACAATTG

CGAAAGGTCATAATGTGATCCTGCTGAATTTCATTACGACCAGTCTAAAA

AGCGCCTGAATTCGCGACCTTCTCGTTACTGACAGGAAAATGGGCCATTG

GCAACCAGGGAAAGATGAACGTGATGATGTTCACAATTTGCTGAATTGTG

GTGATGTGATGCTCACC.

The bacterial host cell having a chromosome which comprises the nucleotide sequence of SEQ ID 2 is in the present invention referred to as XdevK.

In one embodiment of the invention the method for developing the XdevK host cell comprises the steps of:

a) constructing the pRhaBFS plasmid, and b) constructing of the RhaB frame shift mutant.

For constructing the pRhaBFS plasmid the two primers to PCR amplify parts of the rhaBAD operon from the chromosome of the *E. coli* BL21 strain (names of primers in parenthesis) are preferably:

(SBamHI1680 - SEQ ID 19)
5' GTACGCTAGGATCCTGTGGCAGCAACTGATTC 3'

(BSalI1681 - SEQ ID 20)
5' GTAGATAGGTCGACAGCGATCGTCATTGGGAT 3'

The following embodiments are also covered:

1. DNA construct suitable for expressing a recombinant protein in a bacterial host cell, wherein said DNA construct comprises nucleotide sequences encoding:
   - rhaBAD promoter,
   - RhaR transcription activator,
   - RhaS transcription activator,
   - an antibiotic resistance marker,
   - a promoter operably linked to the nucleotide sequence encoding the antibiotic resistance marker,
   - rrnB T1 terminator,
   - rrnB T2 terminator, and
   - a pMB1 origin of replication.
2. DNA construct according to embodiment 1, wherein
   - the antibiotic resistance marker is a kanamycin resistance marker, preferably a kanamycin resistance marker comprising the nucleotide sequence of SEQ ID 12 or a sequence with at least 90% sequence identity thereto;
   - the promoter operably linked to the nucleotide sequence encoding the antibiotic resistance marker is an AmpR promoter, preferably an AmpR promoter comprising the nucleotide sequence of SEQ ID 13 or a sequence with at least 90% sequence identity thereto;
   - the rrnB T1 terminator comprises a nucleotide sequence of SEQ ID 14 or a sequence with at least 90% sequence identity thereto;
   - the rrnB T2 terminator comprises the nucleotide sequence of SEQ ID 15 or a sequence with at least 90% sequence identity thereto; and/or
   - the pMB1 origin of replication comprises the nucleotide sequence of SEQ ID 16 or a sequence with at least 90% sequence identity thereto.
3. DNA construct according to embodiment 1 or 2, wherein
   - the antibiotic resistance marker is a kanamycin resistance marker comprising the nucleotide sequence of SEQ ID 12;
   - the promoter operably linked to the nucleotide sequence encoding the antibiotic resistance marker is an AmpR promoter comprising the nucleotide sequence of SEQ ID 13;
   - the rrnB T1 terminator comprises the nucleotide sequence of SEQ ID 14;
   - the rrnB T2 terminator comprises the nucleotide sequence of SEQ ID 15; and/or
   - the pMB1 origin of replication comprises the nucleotide sequence of SEQ ID 16.
4. DNA construct according to any one of embodiments 1-3, wherein:
   - the rhaBAD promoter comprises the nucleotide sequence of SEQ ID 8 or a sequence with at least 90% sequence identity thereto, preferably the nucleotide sequence of SEQ ID 8;

the RhaR transcription activator comprises the nucleotide sequence of SEQ ID 9 or a sequence with at least 90% sequence identity thereto, preferably the nucleotide sequence of SEQ ID 9;

the RhaS transcription activator comprises the nucleotide sequence of SEQ ID 11 or a sequence with at least 90% sequence identity thereto, preferably the nucleotide sequence of SEQ ID 11;

the antibiotic resistance marker is a kanamycin resistance marker comprising the nucleotide sequence of SEQ ID 12 or a sequence with at least 90% sequence identity thereto, preferably the nucleotide sequence of SEQ ID 12;

the AmpR promoter comprises the nucleotide sequence of SEQ ID 13 or a sequence with at least 90% sequence identity thereto, preferably the nucleotide sequence of SEQ ID 13;

the rrnB T1 terminator comprises the nucleotide sequence of SEQ ID 14 or a sequence with at least 90% sequence identity thereto, preferably the nucleotide sequence of SEQ ID 14;

the rrnB T2 terminator comprises the nucleotide sequence of SEQ ID 15 or a sequence with at least 90% sequence identity thereto, preferably the nucleotide sequence of SEQ ID 15; and the pMB1 origin of replication comprises the nucleotide sequence of SEQ ID 16 or a sequence with at least 90% sequence identity thereto, preferably the nucleotide sequence of SEQ ID 16.

5. DNA construct according to any one of embodiments 1-4, wherein the DNA construct comprises a multiple cloning site comprising 17 restriction sites cleavable by restriction enzymes EcoRI, NdeI, NotI, XhoI, PspXI, PaeR71, BbsI, StyI, AvrII, BanI, Acc65I, KpnI, Eco53kI, SacI, BamHI, XbaI, SalI, AccI, PstI, SbfI, SphI and HindIII.

6. DNA construct according to any one of embodiments 1-5, wherein said DNA construct comprises the nucleotide sequence of SEQ ID 1 or a sequence with at least 90% sequence identity thereto, preferably the nucleotide sequence of SEQ ID 1.

7. DNA construct according to any one of embodiments 1-4, further comprising a nucleotide sequence encoding said recombinant protein, wherein the nucleotide sequence encoding the recombinant protein is operably linked to the rhaBAD promoter, wherein said recombinant protein is a monoclonal antibody or fragment thereof; preferably said recombinant protein is ranibizumab or a fragment thereof; and more preferably said recombinant protein is ranibizumab comprising (i) a light chain comprising the amino acid sequence of SEQ ID 3 and/or (ii) a heavy chain comprising the amino acid sequence of SEQ ID 4.

8. DNA construct according to embodiment 7, wherein said nucleotide sequence encoding the recombinant protein comprises (i) a nucleotide sequence encoding the light chain of ranibizumab comprising the sequence of SEQ ID 5 or a sequence with at least 90% sequence identity thereto, and/or (ii) a nucleotide sequence encoding for the heavy chain of ranibizumab comprising the sequence of SEQ ID 6 or a sequence with at least 90% sequence identity thereto; preferably said nucleotide sequence encoding the recombinant protein comprises (i) a nucleotide sequence encoding for the light chain of ranibizumab comprising the sequence of SEQ ID 5, and/or (ii) a nucleotide sequence encoding for the heavy chain of ranibizumab comprising the sequence of SEQ ID 6.

9. DNA construct according to embodiment 8, wherein said nucleotide sequence encoding the recombinant protein further comprises at least one nucleotide sequence encoding a signal peptide which is operably linked in the direction of transcription to either one or both of the nucleotide sequence of SEQ ID 5 and SEQ ID 6, preferably the signal peptide is PelB; more preferably the nucleotide sequence encoding the PelB signal peptide comprises the sequence of SEQ ID 7 or a sequence with at least 90% sequence identity thereto; most preferably the nucleotide sequence encoding the PelB signal peptide comprises the sequence of SEQ ID 7.

10. DNA construct according to embodiment 9, wherein said DNA construct comprises the sequence of SEQ ID 17 or a sequence with at least 90% sequence identity thereto, preferably comprises a sequence of SEQ ID 17.

11. Expression vector comprising the DNA construct according to any one of embodiments 1-10.

12. Bacterial host cell comprising the DNA construct according to any of embodiments 1-10 or the expression vector according to embodiment 11, wherein said bacterial host cell is preferably an *Escherichia coli* cell, more preferably an *E. coli* K-12 cell.

13. Host cell according to embodiment 12, wherein said host cell either comprises (i) a chromosome which comprises a mutation in the nucleotide sequence of the rhaB gene which renders RhaB inactive, or (ii) a chromosome in which the nucleotide sequence encoding RhaB is deleted.

14. Host cell according to embodiment 12 or 13, wherein said host cell is an *Escherichia coli* W3110 cell, preferably comprising a chromosome which comprises a frame shift-mutation in the nucleotide sequence encoding RhaB.

15. Host cell according to any one of embodiment 12-14, wherein said host cell is an *Escherichia coli* W3110 cell comprising a chromosome which comprises the nucleotide sequence of SEQ ID 2 or a sequence with at least 90% sequence identity thereto, preferably the nucleotide sequence of SEQ ID 2; wherein optionally, the chromosome of the host cell further comprises a nucleotide sequence encoding RhaT.

16. Method of producing a recombinant protein comprising the step of exposing the bacterial host cell according to any of embodiments 12-15 to rhamnose, thereby inducing expression of said recombinant protein.

17. Method according to embodiment 16, further comprising the step of recovering the recombinant protein from the bacterial host cell; optionally further comprising one or more step(s) of purifying the recovered recombinant protein, preferably by one or more chromatography steps.

The present invention has multiple aspects, illustrated in examples 1-8 in the below non-limiting EXAMPLES section. It should be understood that these examples, relating to the use of the XdevK host cell and/or the KTXHIS plasmid, while indicating preferred embodiments of the invention, are given by way of illustration only. From the above disclosed embodiments of the invention and the following examples, one skilled in the art can ascertain the essential characteristics of this invention, and without departing from the spirit and scope thereof, can make various changes and modifications of the invention to adapt it to various types of therapeutic antibodies and immunoglobulins. Thus, various modifications of the invention in addition to those shown and described herein will be apparent to those skilled in the art from the foregoing description. Such modifications are also intended to fall within the scope of the appended claims. An example of such a modification is that one or more of the above indicated SEQ IDs 1-18 may be replaced by a sequence with at least 90% sequence identity thereto.

EXAMPLES

Example 1 relates to the construction of the XdevK host cell.

Example 2 relates to the construction of the KTXHIS-PelbLC-PelbHC expression vector.

Example 3 relates to the light and the heavy chains of ranibizumab expressed by the expression vector in example 2.

Example 4 shows the superior titer of ranibizumab produced according to the present invention when compared to the titer of ranibizumab produced by the method described in a prior art document.

Example 5 shows that ranibizumab produced according to the present invention is free of bacteriophages.

Example 6 is a comparative experiment showing superior titratability of the present invention when compared to prior art host cells and/or plasmids.

Example 7 is a comparative experiment showing superior quality, purity and titer of the present invention when compared to prior art host cells and/or plasmids.

Example 8 is a comparative experiment showing superior control of expression of the present invention when compared to prior art host cells and/or plasmids.

Example 1—Strain Development

The XdevK host cell is an *E. coli* W3310 derivative with a frameshift in the chromosomal copy of RhaB making it unable to utilize rhamnose as a carbon source. The XdevK host cell was developed as a strain for a rhamnose inducible system where the nucleotide sequence encoding the recombinant protein of interest is cloned into the KTXHIS plasmid and expressed under the control of a rhamnose inducible promoter.

The starting strain for the XdevK host cell was *E. coli* W3110 and a similar method of producing the XdevK host cell is described in Wilms et al. in the section titled "Construction of the production Strain *E. coli* BW3110" [3].

The method for developing the XdevK host cell comprises the steps of:

c) constructing the pRhaBFS plasmid, and
d) constructing of the RhaB frame shift mutant.

Step (a)—Construction of the pRhaBFS Plasmid

The following two primers were used to PCR amplify parts of the rhaBAD operon from the chromosome of the *E. coli* BL21 strain (names of primers in parenthesis):

```
                              (SBamHI1680 - SEQ ID 19)
5' GTACGCTAGGATCCTGTGGCAGCAACTGATTC 3'

                              (BSalI1681 - SEQ ID 20)
5' GTAGATAGGTCGACAGCGATCGTCATTGGGAT 3'
```

The PCR product was purified and digested with BamHI and SalI and ligated into a pLemo plasmid (such as pLemo described in U.S. Pat. No. 8,138,324) which had been digested with BamHI and SalI. The pLemo plasmid with the insert was then digested with ClaI. The digest was incubated with T4 polymerase to make blunt ends and then ligated. The resulting pLemo plasmid with the inserted rhaBAD operon genomic region with two additional bases was incubated with BamHI and SalI. The fragment containing the rhaBAD operon genomic region with 2 additional bases was purified and ligated with the pmak705 plasmid digested with BamHI and SalI. The plasmid resulting from the ligation was named pRhaBFS and the sequence was verified by sequencing.

Step (b)—Construction of the RhaB Frame Shift Mutant

*E. coli* W3110 cells were transformed with the gene replacement plasmid pRhaBFS and then plated on LB agar vegitone containing chloramphenicol (20 μg/ml) and incubated at 30° C. for 20 hours. A single colony was picked and placed in LB vegitone and grown in 30° C. until the $OD_{600}$ reached 0.5. 5 μl were transferred from the culture to a LB agar vegitone plate containing chloramphenicol (20 μg/ml) and incubated at 43° C. for 16 hours. Colonies were tested for correct insert into the chromosome using PCR. Colonies with correct insert were grown in LB vegitone containing chloramphenicol (20 g/ml) to saturation three times and then grow 20 hours in LB vegitone. One μl was then plated onto a LB vegitone plate. The LB vegitone plate was used as a template for replica plating onto a McConkey agar plate supplemented with 1% Rhamnose to verify that the cells cannot utilize Rhamnose as a carbon source. One colony was picked and grown in LB vegitone (Sigma) and then aliquoted and named XdevK expression strain. The chromosomal copy of the rhaB gene from XdevK was amplified by means of PCR. The PCR product was sequenced and the correct insertion of two bases (CG) was confirmed (see underlined CG bases in SEQ ID 2):

```
GTTGGCCCCGCTCCACGCCAGTAGCGACTCGTCCCAGTCGTCGCTATTGA

TATTGACCAGTTGCGTGGTCGTGGCGTTGGTATATTCCCAGTTCATCTTG

CCGGTCAGGCGATAACTGAAGTAATCCGGCATCAGCAGAGCGTGAGCAAT

GTGTGGAATAAGTTCAGGTTGTTGCTCCGTCAGCGCACGCAACTGATAAA

GCGTATTGAAGGGCAGAAACTGGATGCCGCTACGTTGATAAATATCGCGT

TTGCCGAGTTGTTGTTGTGCCTGCGCCATTAGGCCATTGGTGCGGCTATC

GCGATAAGCAACGGGCAGGCCCACACGCTGACCCTGTTGGTCGAGCAGCA

CAAAGTCCACGCCCCAGGTATCAATCCCAATGCTATCGCGATACGAATCC

CTTCCTCGCACACCTTGTTTAATCCAAGGCGAATGGCACTTTCCAGGCTA

TCCACATCCCAGGTGACATAGCCGTTCTGACTATGCAGCCCATTGTTAAA

ACGATGGATTTCGCGCAGCGTCAGGCTGCGGCATTCACGCTCGTAACGCG

CCAGCATCACGCGCCCACTGGATGCGCCGAGATCGACGGCGACACAATTG

CGAAAGGTCATAATGTGATCCTGCTGAATTTCATTACGACCAGTCTAAAA

AGCGCCTGAATTCGCGACCTTCTCGTTACTGACAGGAAAATGGGCCATTG
```

-continued

```
GCAACCAGGGAAAGATGAACGTGATGATGTTCACAATTTGCTGAATTGTG

GTGATGTGATGCTCACC
```

Example 2—KTXHIS-PelbLC-PelbHC

Figure 3:
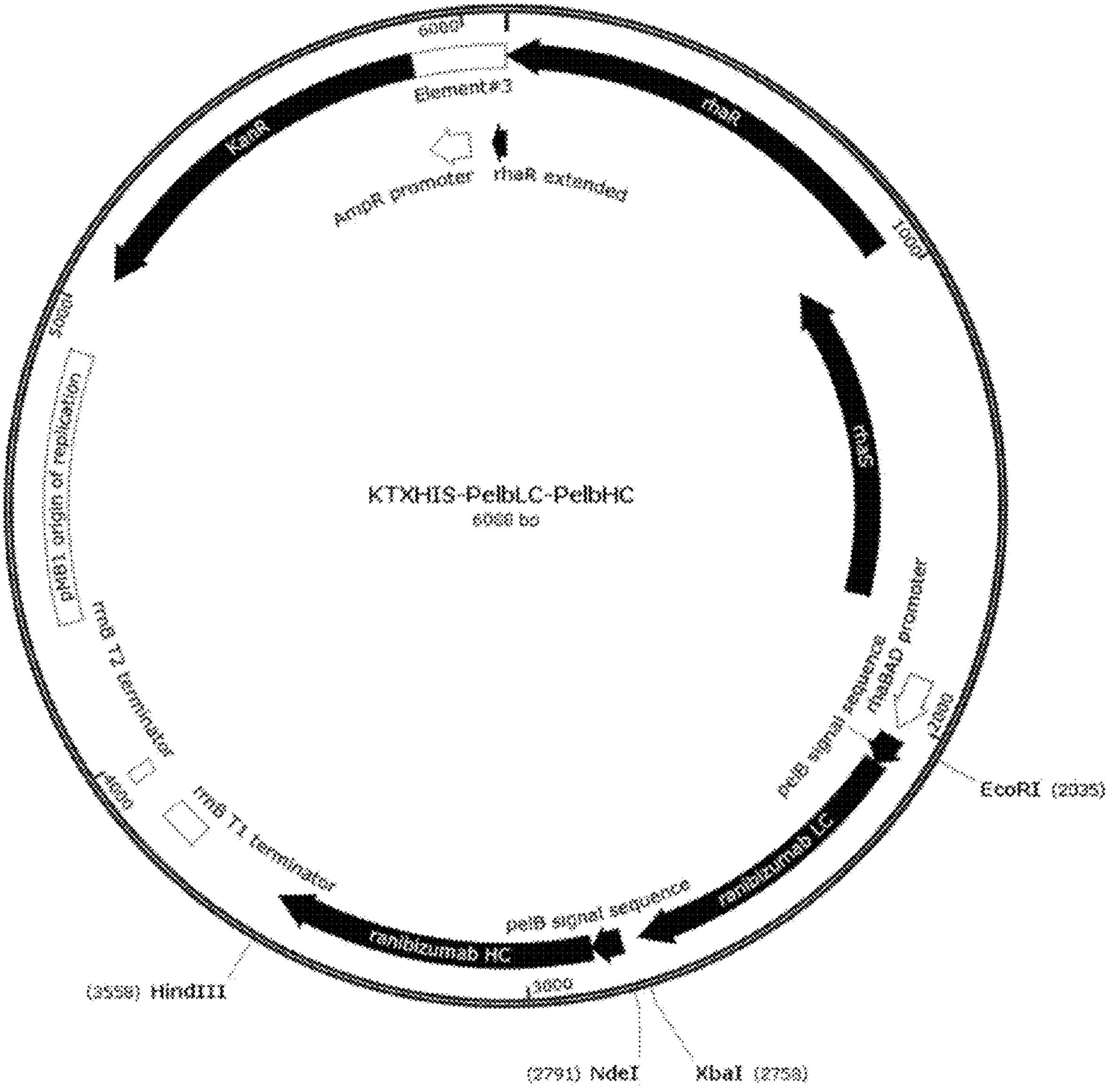
FIG. 3—Plasmid map of KTXHIS-PelbLC-PelbHC

The PelB signal peptide comprising the nucleotide sequence of SEQ ID 7 was fused in front of nucleic acids encoding both the light and the heavy chains of ranibizumab and then cloned into the KTXHIS expression plasmid. The resulting nucleotide sequence comprises a nucleotide sequence of SEQ ID 17 and is referred to as KTXHIS-PelbLC-PelbHC in the present invention. Moreover, the plasmid map of KTXHIS-PelbLC-PelbHC is illustrated in FIG. 3.

The nucleotide sequence of SEQ ID 17 is disclosed below and the sequence of the nucleic acid encoding the light chain fused to PelB signal sequence is underlined and the sequence of the nucleic acid encoding the heavy chain fused to PelB signal sequence is in bold (see also FIG. 3 for the arrangement of PelB with respect to light and heavy chains of ranibizumab):

```
ATCTTTCTGCGAATTGAGATGACGCCACTGGCTGGGCGTCATCCCGGTTTCCCGG

GTAAACACCACCGAAAAATAGTTACTATCTTCAAAGCCACATTCGGTCGAAATAT

CACTGATTAACAGGCGGCTATGCTGGAGAAGATATTGCGCATGACACACTCTGAC

CTGTCGCAGATATTGATTGATGGTCATTCCAGTCTGCTGGCGAAATTGCTGACGC

AAAACGCGCTCACTGCACGATGCCTCATCACAAAATTTATCCAGCGCAAAGGGAC

TTTTCAGGCTAGCCGCCAGCCGGGTAATCAGCTTATCCAGCAACGTTTCGCTGGA

TGTTGGCGGCAACGAATCACTGGTGTAACGATGGCGATTCAGCAACATCACCAAC

TGCCCGAACAGCAACTCAGCCATTTCGTTAGCAAACGGCACATGCTGACTACTTT

CATGCTCAAGCTGACCAATAACCTGCCGCGCCTGCGCCATCCCCATGCTACCTAA

GCGCCAGTGTGGTTGCCCTGCGCTGGCGTTAAATCCCGGAATCGCCCCCTGCCAG

TCAAGATTCAGCTTCAGACGCTCCGGGCAATAAATAATATTCTGCAAAACCAGAT

CGTTAACGGAAGCGTAGGAGTGTTTATCATCAGCATGAATGTAAAAGAGATCGCC

ACGGGTAATGCGATAAGGGCGATCGTTGAGTACATGCAGGCCATTACCGCGCCA

GACAATCACCAGCTCACAAAAATCATGTGTATGTTCAGCAAAGACATCTTGCGGA

TAACGGTCAGCCACAGCGACTGCCTGCTGGTCGCTGGCAAAAAAATCATCTTTGA

GAAGTTTTAACTGATGCGCCACCGTGGCTACCTCGGCCAGAGAACGAAGTTGATT

ATTCGCAATATGGCGTACAAATACGTTGAGAAGATTCGCGTTATTGCAGAAAGCC

ATCCCGTCCCTGGCGAATATCACGCGGTGACCAGTTAAACTCTCGGCGAAAAAGC

GTCGAAAAGTGGTTACTGTCGCTGAATCCACAGCGATAGGCGATGTCAGTAACGC

TGGCCTCGCTGTGGCGTAGCAGATGTCGGGCTTTCATCAGTCGCAGGCGGTTCAG

GTATCGCTGAGGCGTCAGTCCCGTTTGCTGCTTAAGCTGCCGATGTAGCGTACGC

AGTGAAAGAGAAAATTGATCCGCCACGGCATCCCAATTCACCTCATCGGCAAAAT

GGTCCTCCAGCCAGGCCAGAAGCAAGTTGAGACGTGATGCGCTGTTTTCCAGGTT

CTCCTGCAAACTGCTTTTACGCAGCAAGAGCAGTAATTGCATAAACAAGATCTCG

CGACTGGCGGTCGAGGGTAAATCATTTTCCCCTTCCTGCTGTTCCATCTGTGCAAC

CAGCTGTCGCACCTGCTGCAATACGCTGTGGTTAACGCGCCAGTGAGACGGATAC

TGCCCATCCAGCTCTTGTGGCAGCAACTGATTCAGCCCGGCGAGAAACTGAAATC

GATCCGGCGAGCGATACAGCACATTGGTCAGACACAGATTATCGGTATGTTCATA

CAGATGCCGATCATGATCGCGTACGAAACAGACCGTGCCACCGGTGATGGTATA

GGGCTGCCCATTAAACACATGAATACCCGTGCCATGTTCGACAATCACAATTTCA

TGAAAATCATGATGATGTTCAGGAAAATCCGCCTGCGGGAGCCGGGGTTCTATCG

CCACGGACGCGTTACCAGACGGAAAAAAATCCACACTATGTAATACGGTCATACT

GGCCTCCTGATGTCGTCAACACGGCGAAATAGTAATCACGAGGTCAGGTTCTTAC
```

-continued

CTTAAATTTTCGACGGAAAACCACGTAAAAAACGTCGATTTTTCAAGATACAGCG

TGAATTTTCAGGAAATGCGGTGAGCATCACATCACCACAATTCAGCAAATTGTGA

ACATCATCACGTTCATCTTTCCCTGGTTGCCAATGGCCCATTTTCTTGTCAGTAAC

GAGAAGGTCGCGAATCCAGGCGCTTTTTAGACTGGTCGTAATGAAATTCAGGAGG

AATTCCTAATGAAATATCTGCTGCCGACCGCAGCAGCGGGTCTGCTGCTGCTGGC

AGCACAGCCTGCAATGGCAGATATTCAGCTGACCCAGAGCCCGAGCAGCCTGAG

CGCAAGCGTTGGTGATCGTGTTACCATTACCTGTAGCGCAAGCCAGGATATTAGC

AATTATCTGAATTGGTATCAGCAGAAACCGGGTAAAGCACCGAAAGTGCTGATCT

ATTTTACCAGCAGCCTGCATAGCGGTGTTCCGAGCCGTTTTAGCGGTAGCGGTAG

TGGCACCGATTTTACCCTGACCATTAGCAGCCTGCAGCCGGAAGATTTTGCAACC

TATTATTGTCAGCAGTATAGCACCGTTCCGTGGACCTTTGGTCAGGGCACCAAAG

TTGAAATTAAACGTACCGTTGCAGCACCGAGCGTTTTTATCTTTCCGCCTAGTGAT

GAACAGCTGAAAAGCGGCACCGCAAGCGTTGTTTGTCTGCTGAATAACTTTTATC

CGCGTGAAGCAAAAGTTCAGTGGAAAGTTGATAATGCACTGCAGAGCGGTAATA

GCCAAGAAAGCGTTACCGAACAGGATAGCAAAGATAGCACCTATAGCCTGAGCA

GCACCCTGACCCTGAGCAAAGCAGATTATGAAAAACACAAAGTGTATGCCTGCG

AAGTTACCCATCAGGGTCTGAGCAGTCCGGTTACCAAAAGTTTTAATCGTGGTGA

ATGCTAATAATCTAGAACTGTTATCGATATCAGGAGGATTAGCATATGAAATATC

TGCTGCCGACCGCAGCAGCGGGTCTGCTGCTGCTGGCAGCACAGCCTGCAA

TGGCAGAAGTTCAGCTGGTTGAAAGCGGTGGTGGTCTGGTTCAGCCTGGTG

GTAGCCTGCGTCTGAGCTGTGCAGCAAGCGGTTATGATTTTACCCATTATGG

TATGAATTGGGTTCGTCAGGCACCGGGTAAAGGTCTGGAATGGGTTGGTTG

GATTAATACCTATACCGGTGAACCGACCTATGCAGCAGATTTTAAACGTCGT

TTTACCTTTAGCCTGGATACCAGCAAAAGCACCGCATATCTGCAGATGAATA

GCCTGCGTGCAGAGGATACCGCAGTGTATTATTGTGCAAAATATCCGTATTA

TTACGGCACCAGCCATTGGTATTTCGATGTTTGGGGTCAGGGCACCCTGGTT

ACCGTTAGCAGCGCAAGCACCAAAGGTCCGAGCGTTTTTCCGCTGGCACCG

AGCAGCAAAAGTACCAGCGGTGGCACCGCAGCACTGGGTTGTCTGGTTAAA

GATTATTTTCCGGAACCGGTTACCGTGAGCTGGAATAGCGGTGCACTGACCA

GCGGTGTTCATACCTTTCCGGCAGTTCTGCAGAGCAGCGGTCTGTATAGCCT

GAGCAGCGTTGTTACCGTTCCGAGCAGCAGCCTGGGCACCCAGACCTATATT

TGTAATGTTAATCATAAACCGAGCAATACCAAAGTGGATAAAAAAGTGGAAC

CGAAAAGCTGCGATAAAACCCATCTGTAATAAAAGCTTGGCTGTTTTGGCGGA

TGAGAGAAGATTTTCAGCCTGATACAGATTAAATCAGAACGCAGAAGCGGTCTG

ATAAAACAGAATTTGCCTGGCGGCAGTAGCGCGGTGGTCCCACCTGACCCCATGC

CGAACTCAGAAGTGAAACGCCGTAGCGCCGATGGTAGTGTGGGGTCTCCCCATGC

GAGAGTAGGGAACTGCCAGGCATCAAATAAAACGAAAGGCTCAGTCGAAAGACT

GGGCCTTTCGTTTTATCTGTTGTTTGTCGGTGAACGCTCTCCTGAGTAGGACAAAT

CCGCCGGGAGCGGATTTGAACGTTGCGAAGCAACGGCCCGGAGGGTGGCGGGCA

GGACGCCCGCCATAAACTGCCAGGCATCAAATTAAGCAGAAGGCCATCCTGACG

-continued

GATGGCCTTTTTGCGTTTCTACAAACTCTTTTGTTTATTTTTCTAAATACATTCAAA

TATGTATCCGCTCATGAGACTAGGCTTCCGCGCCCTCATCCGAAAGGGCGTATTC

ATATATGCGGTGTGAAATACCGCACAGATGCGTAAGGAGAAAATACCGCATCAG

GCGCTCTTCCGCTTCCTCGCTCACTGACTCGCTGCGCTCGGTCGTTCGGCTGCGGC

GAGCGGTATCAGCTCACTCAAAGGCGGTAATACGGTTATCCACAGAATCAGGGG

ATAACGCAGGAAAGAACATGTGAGCAAAAGGCCAGCAAAAGGCCAGGAACCGT

AAAAAGGCCGCGTTGCTGGCGTTTTTCCATAGGCTCCGCCCCCCTGACGAGCATC

ACAAAAATCGACGCTCAAGTCAGAGGTGGCGAAACCCGACAGGACTATAAAGAT

ACCAGGCGTTTCCCCCTGGAAGCTCCCTCGTGCGCTCTCCTGTTCCGACCCTGCCG

CTTACCGGATACCTGTCCGCCTTTCTCCCTTCGGGAAGCGTGGCGCTTTCTCATAG

CTCACGCTGTAGGTATCTCAGTTCGGTGTAGGTCGTTCGCTCCAAGCTGGGCTGTG

TGCACGAACCCCCCGTTCAGCCCGACCGCTGCGCCTTATCCGGTAACTATCGTCTT

GAGTCCAACCCGGTAAGACACGACTTATCGCCACTGGCAGCAGCCACTGGTAAC

AGGATTAGCAGAGCGAGGTATGTAGGCGGTGCTACAGAGTTCTTGAAGTGGTGG

CCTAACTACGGCTACACTAGAAGGACAGTATTTGGTATCTGCGCTCTGCTGAAGC

CAGTTACCTTCGGAAAAAGAGTTGGTAGCTCTTGATCCGGCAAACAAACCACCGC

TGGTAGCGGTGGTTTTTTTGTTTGCAAGCAGCAGATTACGCGCAGAAAAAAAGGA

TCTCAAGAAGATCCTTTGATCTTTTCTACGGGGTCTGACGCTCAGTGGAACGAAA

ACTCACGTTAAGGGATTTTGGTCATGAGATTATCAAAAAGGATCTTCACCTAGAT

CCTTTTAAATTAAAAATGAAGTTTTAAATCAATCTAAAGTATATATGAGTAAACT

TGGTCTGACAGTTAGAAAAACTCATCGAGCATCAAATGAAACTGCAATTTATTCA

TATCAGGATTATCAATACCATATTTTTGAAAAAGCCGTTTCTGTAATGAAGGAGA

AAACTCACCGAGGCAGTTCCATAGGATGGCAAGATCCTGGTATCGGTCTGCGATT

CCGACTCGTCCAACATCAATACAACCTATTAATTTCCCCTCGTCAAAAATAAGGT

TATCAAGTGAGAAATCACCATGAGTGACGACTGAATCCGGTGAGAATGGCAAAA

GTTTATGCATTTCTTTCCAGACTTGTTCAACAGGCCAGCCATTACGCTCGTCATCA

AAATCACTCGCATCAACCAAACCGTTATTCATTCGTGATTGCGCCTGAGCGAGAC

GAAATACGCGATCGCTGTTAAAAGGACAATTACAAACAGGAATCGAATGCAACC

GGCGCAGGAACACTGCCAGCGCATCAACAATATTTTCACCTGAATCAGGATATTC

TTCTAATACCTGGAATGCTGTTTTCCCGGGGATCGCAGTGGTGAGTAACCATGCA

TCATCAGGAGTACGGATAAAATGCTTGATGGTCGGAAGAGGCATAAATTCCGTCA

GCCAGTTTAGTCTGACCATCTCATCTGTAACATCATTGGCAACGCTACCTTTGCCA

TGTTTCAGAAACAACTCTGGCGCATCGGGCTTCCCATACAATCGATAGATTGTCG

CACCTGATTGCCCGACATTATCGCGAGCCCATTTATACCCATATAAATCAGCATC

CATGTTGGAATTTAATCGCGGCCTAGAGCAAGACGTTTCCCGTTGAATATGGCTC

ATACTCTTCCTTTTTCAATATTATTGAAGCATTTATCAGGGTTATTGTCTCATGAG

CGGATACATATTTGAATGTATTTAGAAAAATAAACAAATAGGGGTTCCGCGCACA

TTTCCCCGAAAAGTGCCACCTGACGTCTAAGAAACCATTATTATCATGACATTAA

CCTATAAAAATAGGCGTATCACGAGGCCCTTTCGTCT

Example 3—Recombinant Protein—Ranibizumab

The amino acid sequence of the light chain of ranibizumab expressed by the expression vector KTXHIS-PelbLC-PelbHC comprises the sequence of SEQ ID 3:

DIQLTQSPSSLSASVGDRVTITCSASQDISNYLNWYQQKPGKAPKVLIYF

TSSLHSGVPSRFSGSGSGTDFTLTISSLQPEDFATYYCQQYSTVPWTFGQ

GTKVEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC

The amino acid sequence of the heavy chain of ranibizumab expressed by the expression vector KTXHIS-PelbLC-PelbHC comprises the sequence of SEQ ID 4:

EVQLVESGGGLVQPGGSLRLSCAASGYDFTHYGMNWVRQAPGKGLEWVGW

INTYTGEPTYAADFKRRFTFSLDTSKSTAYLQMNSLRAEDTAVYYCAKYP

YYYGTSHWYFDVWGQGTLVTVSSASTKGPSVFPLAPSSKSTSGGTAALGC

LVKDYFPEPVTVSWNSGALTSGVHTFPAVLQSSGLYSLSSVVTVPSSSLG

TQTYICNVNHKPSNTKVDKKVEPKSCDKTHL

Moreover, the resulting PelB signal peptide comprises an amino acid sequence of SEQ ID 18 [6]: MKYLLPTAAAGLLLLAAQPAMA Example 4—Superior Titer of Ranibizumab Produced According to the Present Invention Compared to Prior Art Titer 3 different batches comprising ranibizumab were produced according to the below described method.

Minimal media was prepared and inoculated with overnight culture of the XdevK host cell comprising the expression vector KTXHIS-PelbLC-PelbHC from a shake flask. Fermentation temperature was set to 30° C. and the cultures were grown for 22 h in batch phase. This phase was followed by a growth phase for 10 h. The temperature was adjusted to 28.5° C. and the growth rate was then decreased by controlling the glucose feed. The culture was induced with 500 μM of rhamnose injected into the fermenter. The glucose feed was also supplemented with rhamnose for continuous induction throughout the induction phase. Material was harvested after 36 h of induction. The total fermentation time was 68 h and harvested volume was 8530 ml.

After harvest, all material, media and cells, were homogenized. 5500 ml were stored in −80° C. and 3000 ml were clarified and washed using TFF. The cells were washed with a volume three times the initial volume for increased release of the product. The resulting product comprising ranibizumab was purified by using capto L affinity chromatography which is also the chromatography method used in Kumar et al. 141 (see sections 2.4 and 3.2 in Kumar et al.) and then the concentration of purified ranibizumab was determined.

The first, second and third batches comprised a ranibizumab titer of 531 mg/L, 487 mg/L and 518 mg/L, respectively.

Figure 6:
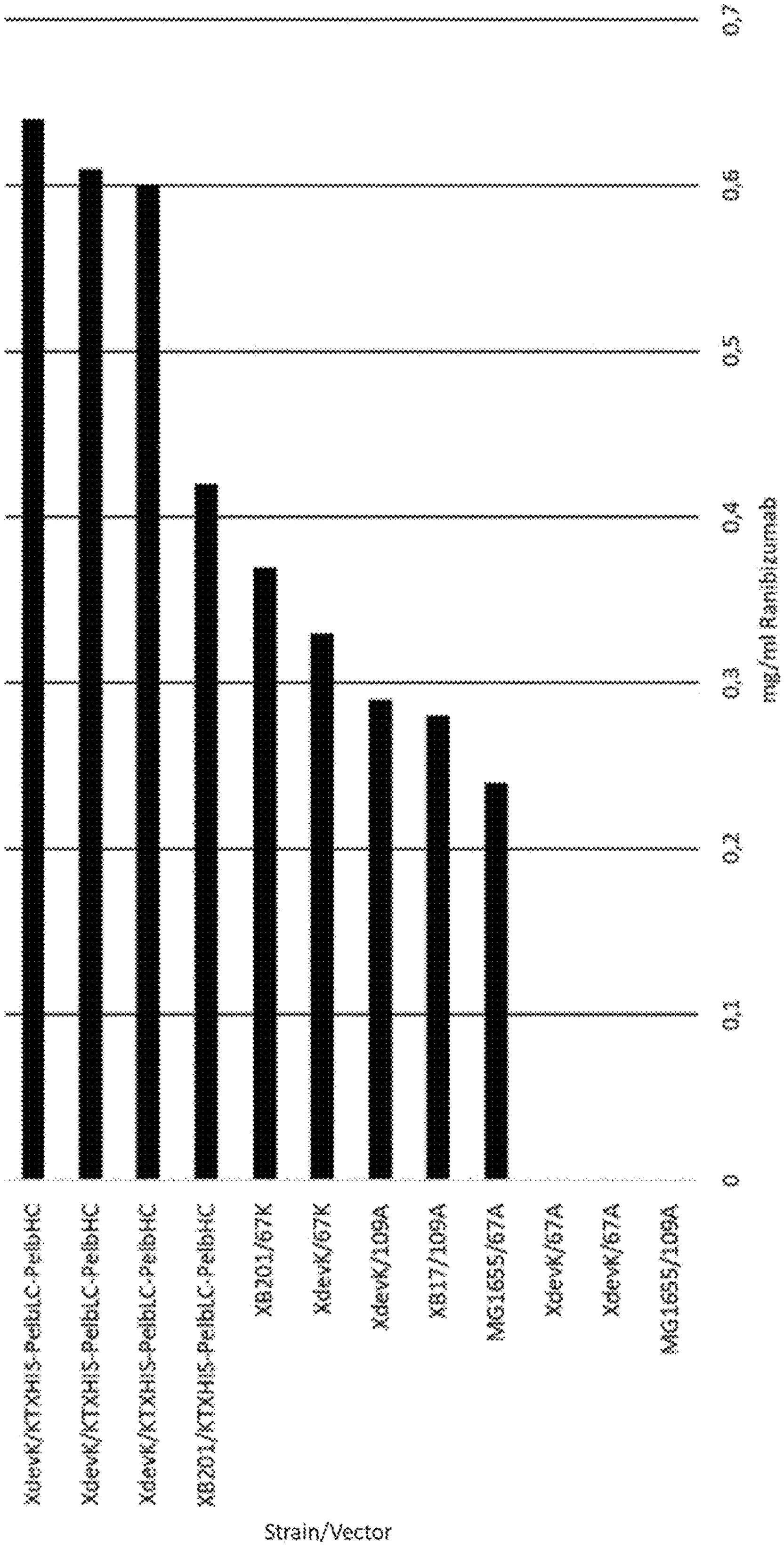
FIG. 6—Summary of Affinity HPLC titer data

As a comparison, in prior art document Kumar et al (which discloses similar purification methods), the ranibizumab titer ranges from 5 mg/L to 25 mg/L as indicated in FIG. 6 and the Abstract of this document [4].

Consequently, the method according to the present invention (as well as the use of XdevK host cell and expression vector KTXHIS-PelbLC-PelbHC therein) provides unexpectedly higher levels of ranibizumab titer when compared to prior art methods.

Example 5—Cell Banking

The XdevK was transformed with KTXHIS-PelbLC-PelbHC. A single colony was picked and grown in Defined Bioreactor Medium (DBM) overnight, the following day 20% glycerol was added, the culture was aliquoted and stored in −80° C. One aliquot (50 μl) was used to inoculate 100 ml of Defined Bioreactor Medium (DBM) and cultured for 24 h in 30° C., temperature was shifted to 35° C. and the cells were cultured for an additional 6 h to increase OD. OD A600 nm=4.44. 20% of glycerol was added, culture was aliquoted (100 μl aliquots) and frozen in −80° C. as RCB100.

Aliquots of the strain were sent for phage testing and microbial purity testing at Charles River Laboratories. The report stated: "It was concluded that RCB100 is free of bacteriophage when tested for both lysogenic prophage and free bacteriophage. The limit of the number of free bacteriophage is less than 1 plaque forming unit per mL of an overnight culture."

Example 6—Comparative Experiments Showing Superior Titratability

Materials and Methods

The following three strains were used in the comparative experiments:

1. XdevK host cell described in above Example 1; in other words, it is a strain which:
   has a W3110 strain background having a genotype of: F-, λ-, IN(rrnD-rrnE)1, rph-1);
   is a K-strain derivative and contains a mutation in the RhaB gene, making it unable to degrade Rhamnose and to use Rhamnose as a carbon source.
2. XB210 described in Hjelm et al. [2] which:
   is a BL21 (DE3) strain having a genotype: F-dompt hsdSB (rB-, mB-) gal dcm (DE3));
   is a B-strain derivative and contains a mutation in the RhaB gene and a deletion of the Rhamnose transporter gene (RhaT), making it unable to actively transport, degrade Rhamnose and to use Rhamnose as a carbon source;
   contains parts of the DE3 prophage inserted into the chromosome and does not express the ion protease or the OmpT protease; and
3. MG1655 described in Giacalone et al. [5] which is an *E. coli* wild type K-strain.

The following four expression plasmids were used to express the nucleic acid sequence for ranibizumab, i.e. sequences encoding the heavy and light chains of ranibizumab were cloned into the following expression plasmids:

1. KTXHIS;
2. pRha109A described in Giacalone et al. [5];
3. pRha67A described in Giacalone et al. [5]; and
4. pRha67K described in Hjelm et al. [2].

The resulting expression vectors were confirmed by full sequencing.

Moreover, the resulting expression vectors were introduced into the XdevK, XB201 and MG1655 strains (i.e. host cells) to test the different combinations of strains and plasmids to understand the influence on titratability, titer, quality and control of expression.

Experimental Setup for Titratability Comparisons

The expression vectors comprising the heavy and light chains of ranibizumab were transformed into XdevK, XB201 and MG1655 using standard protocols. Overnight cultures were prepared by inoculating a single colony in 3 ml of LB-veg liquid media containing 100 μg/ml ampicillin or 50 μg/ml kanamycin depending on the construct. Cultures were incubated in a 15 ml falcon tube at 37° C. with shaking for 16 hours. Cultures were then back-diluted (1:50) into 5 ml of LB-veg plus antibiotics in a 24-well growth plate, and incubated as before until an OD600 of approximately 0.3-0.5 was reached. Expression was induced by addition of 5, 50, 100, 250, 500, 5000 μM rhamnose and incubation for 5 hours at 30° C. with shaking followed. A volume of cells corresponding to an OD600 of 0.2 units was collected, resuspended in 20 μl 2× Laemlli loading buffer, boiled for 5 mins after which 7.5 μl was analyzed by 12% mini SDS-PAGE. The gel was then immediately transferred to a nitrocellulose/PVDF membrane and probed using anti-Fab antibody for Western blot analysis.

Results and Discussion—Titratability

FIGS. 4*a*, 4*b*, 4*c* and 4*d* show the Western blots for the titratability comparisons. Each of the control lanes is loaded with purified ranibizumab.

FIG. 4*a* shows:

- the accumulation of expressed ranibizumab in strain XdevK in combination with KTXHIS-PelbLC-PelbHC; and
- the accumulation of expressed ranibizumab in strain XdevK in combination with the expression vector based on the pRha67K (67K) plasmid.

FIG. 4*b* shows:

- the accumulation of expressed ranibizumab in strain XB201 in combination with the expression vector based on the pRha67K (67K) plasmid; and
- the accumulation of expressed ranibizumab in strain XdevK in combination with the expression vector based on the pRha67A (67A) plasmid.

FIG. 4*c* shows:

- the accumulation of expressed ranibizumab in strain XdevK in combination with the expression vector based on the pRha109A (109A) plasmid; and
- the accumulation of expressed ranibizumab in strain MG1655 in combination with the expression vector based on the pRha67A (67A) plasmid.

FIG. 4*d* shows:

- repeating of the experiment showing the accumulation of expressed ranibizumab in strain XdevK in combination with KTXHIS-PelbLC-PelbHC in order to visualize the titratability in combined use of XdevK and the KTXHIS-PelbLC-PelbHC setup.

FIGS. 4*a*, 4*b*, 4*c* and 4*d* clearly and unambiguously show that the setup with XdevK in combination with KTXHIS-PelbLC-PelbHC has superior technical effect to the other setups when comparing titratability because:

- the expression of ranibizumab increases gradually for XdevK/KTXHIS-PelbLC-PelbHC each addition of 5, 50, 100, 250, 500, 5000 μM rhamnose; and
- the expression of ranibizumab does not increase gradually in any other combinations—see for example the combination of XB201/67K which gives rise to a "shoulder, i.e. gradual increase but then gradual decrease.

Figure 4A:
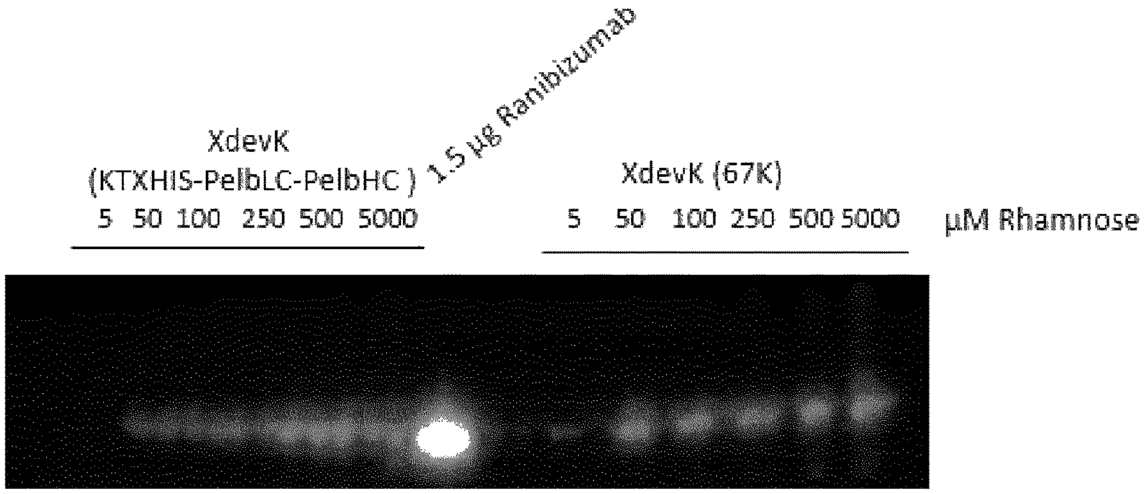
FIG. 4*a*-4*d*—Western blots using anti-FAB antibody—Titratability comparison in small scale experiments.
Figure 4B:
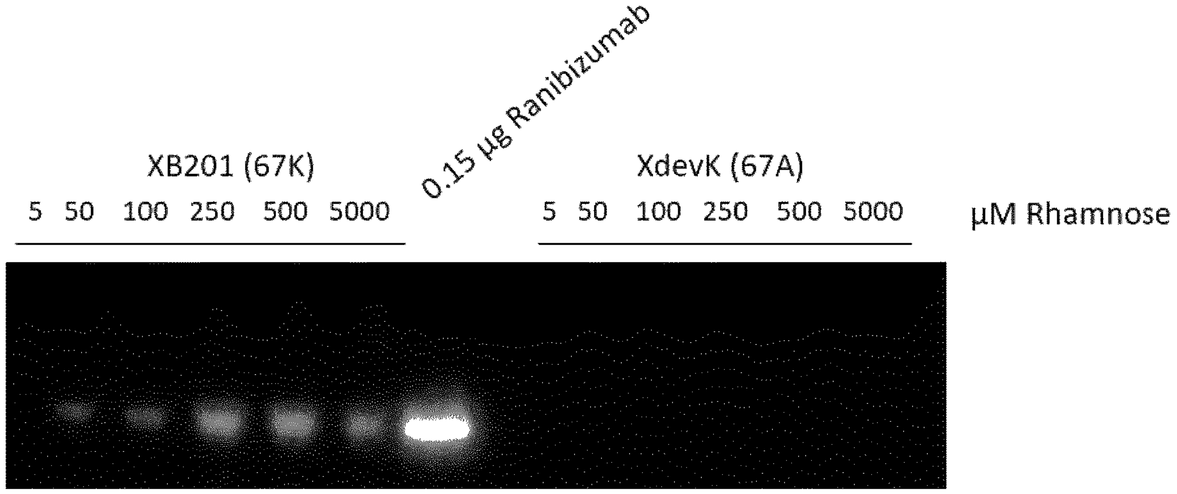
Figure 4C:
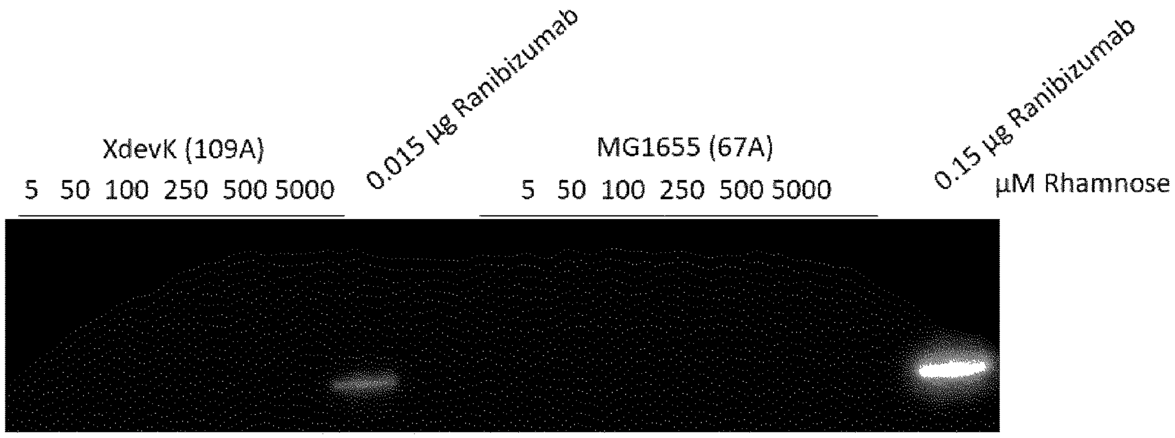
Figure 4D:
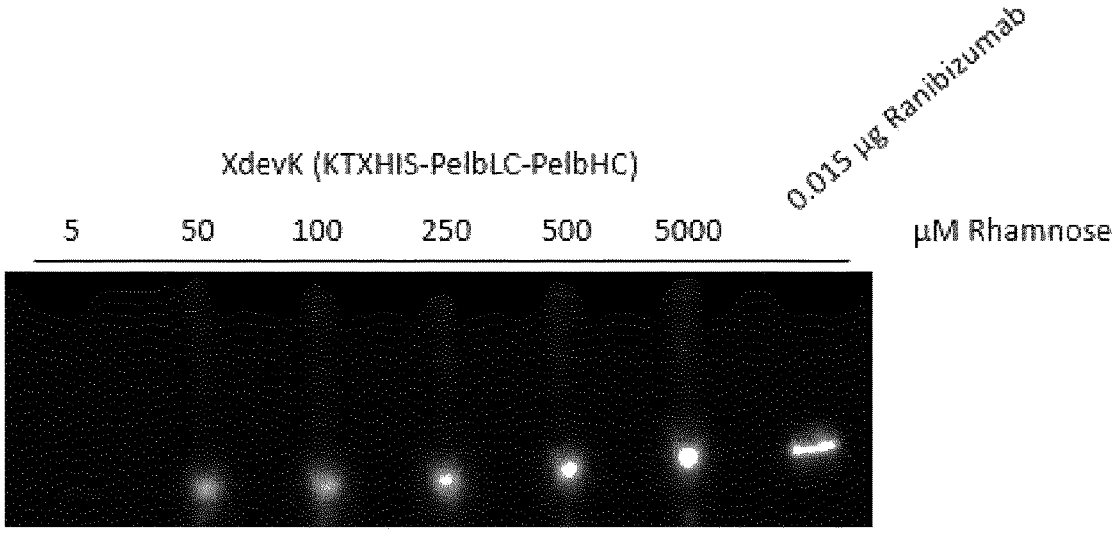

Furthermore, FIGS. 4*a*, 4*b*, 4*c* also show that the cells harboring the expression vectors based on the pRha109A or pRha67A plasmids accumulated very little ranibizumab, at least 100-fold less than the other setups using either KTXHIS-PelbLC-PelbHC or the expression vector based on the pRha67K plasmid (wherein the said fold change was observed by comparing amount of positive control loaded).

It should be noted that the combinations of:

- MG1655 and the expression vectors based on the pRha109A plasmid (see FIG. 6),
- MG1655 and the expression vectors based on the pRha67K plasmid (see FIG. 7*b*),
- MG1655 and KTXHIS-PelbLC-PelbHC (see FIG. 7*b*), did not give rise to detectable production of ranibizumab and therefore titratability experiments were not conducted for said combinations.

Hence, in conclusion, the XdevK in combination with KTXHIS-PelbLC-PelbHC provides a superior titratability compared to the setups known from prior art. Thus, this allows for a precisely tuning of recombinant protein production rates and therefore the recombinant protein production rates can be set precisely and stably.

Example 7—Comparative Experiments Showing Superior Quality and Titer

Experimental Setup for Titer and Quality Experiments

The expression vectors comprising the heavy and light chains of ranibizumab were transformed into XdevK, XB201 and MG1655 using standard protocols to produce Research Cell Bank (RCB) of respective combination of strain and plasmid. Pre-culture (in shake flask) was inoculated from a single vial of RCB and grown overnight (O/N) in defined reactor media; Potassium dihydrogen phosphate ($KH_2PO_4$) 4.5 g/L, di-Potassium hydrogen phosphate ($K_2HPO_4$) 3.0 g/L. Ammonium sulfate ($(NH_4)_2SO_4$) 3.75 g/L, tri-Sodium citrate dihydrate ($HOC(COONa)(CH_2COONa)_2 \cdot 2H_2O$) 1.88 g/L, Iron(III) chloride hexahydrate ($FeCl_3 \cdot 6H_2O$) 0.0525 g/L, Zinc sulfate heptahydrate ($ZnSO_4 \cdot 7H_2O$) 0.0158 g/L, Copper(II) sulfate pentahydrate ($CuSO_4 \cdot 5H_2O$) 0.00397 g/L, Manganese sulfate monohydrate ($MnSO_4 \cdot 1H_2O$) 0.0198 g/L, Calcium chloride dihydrate ($(CaCl_2) \cdot 2H_2O$) 0.0207 g/L add 17.1 mL sterile 60% (v/w) glucose solution, 2.432 mL 2.5 M $MgSO_4 \cdot 7H_2O$, 1 mL 50 mg/mL Kanamycin solution. The pH was adjusted by adding 1.5 mL 25% ammonium hydroxide solution (to ca. 6.95). A DAS box fermenter was prepared with defined reactor media and inoculated with O/N pre-culture. The cells growth was controlled by feeding the culture with 60% (v/w) sterile glucose. Production phase was initiated by the addition of rhamnose as the inducer. If necessary, the feed profile was adjusted and salts were added to the culture. The cells were harvested after 20-42 h of induction followed by batch purification. The harvest samples were added to a 96-well deep-well microtiter plate that contained wells with pre-frozen water to guarantee cooling of the sample. Empty wells were filled with MilliQ water (MQ). Sonication was performed using a 24-element probe on a sonics vibra-cell device for 3 cycles of 20 sec each at an amplitude of 40% with 30 sec pause in-between cycles. The sonicated samples were transferred to 2 mL spin tubes and centrifuged for 20 min at 20 000× g at 4° C. in a centrifuge 5430 R. The supernatant was removed carefully by pipetting and added to a 50% slurry of the pre-equilibrated Capto L affinity resin. Equilibration had been performed three times with 20 mM sodium phosphate, 150 mM NaCl, pH 7.2 (EQ). 1.9 mL of supernatant was used to load 100 μL of Capto L slurry, which corresponds to a load rate of 9.5 mL/mL resin. The supernatant and the resin were incubated for 15 min at room temperature (RT) while shaking at 1500 rpm on a Thermo-Mixer C followed by centrifugation for 1 min at 2000× g at RT. The supernatants were discarded. The resin was washed twice by adding 500 μL of EQ and separating the resin by centrifugation at 2000×g, as above. During the third wash step using 300 μL of EQ, the resin was transferred to cellulose acetate filter spin cups suitable for 400 μL and centrifuged as above. The fourth wash step was performed with 150 μL EQ. The spin cups were transferred to new collection tubes and elution with 50 mM sodium acetate pH 3.0 was performed in three cycles using 0.4 μL of per μL resin in total (e.g. 3×40 μL for 50 μL slurry used). The protein concentration in the eluates was analyzed using an affinity HPLC setup. The quality of the samples was analyzed by SDS-PAGE and SCX-HPLC.

Results and Discussion for Titer and Quality Experiments

Figure 5:
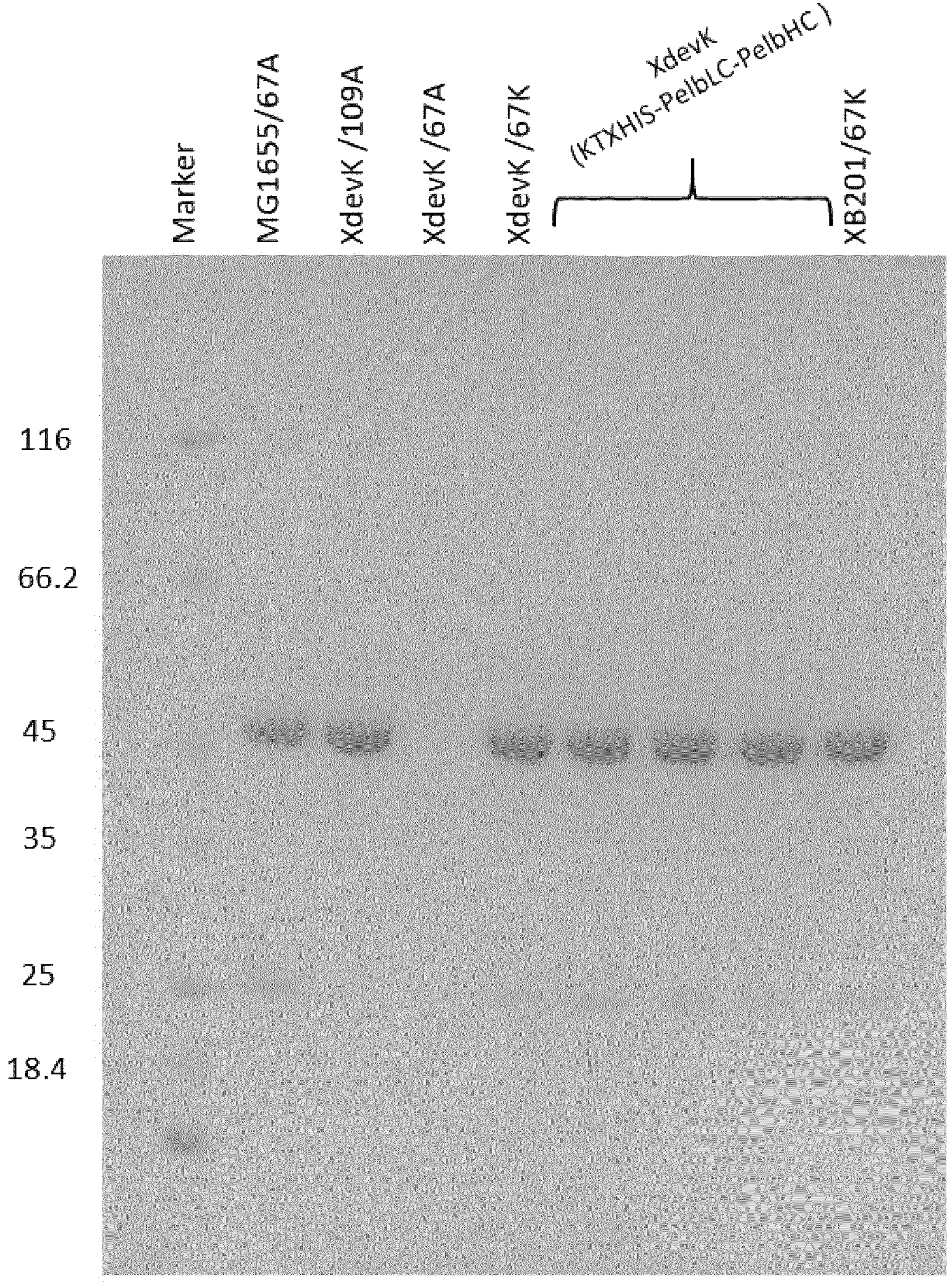
FIGS. 5—Small-scale batch purification from clarified homogenized lysate samples from harvested material with Capto L resin western blot using anti-FAB antibody. Gel loading: 3 μg product applied except for XB17/67A (only 0.2 μg product applied due to low yield). Marker from 18.4-116 kDa.

Samples were analyzed using SDS-PAGE as illustrated in FIG. 5. No detectable quality difference, no increased banding pattern or increased amounts of free light chain or heavy chain, could be detected. However, the setup using the XdevK strain in combination with the expression vector based on the pRha67A plasmid gave very little material and no band could be detected. Furthermore, the setup using strain XdevK in combination with the expression vector based on the pRha109A plasmid grew very poorly and was therefore harvested after a shorter induction time (of 20 hours whereas all other samples were harvested after 42 hours).

The amount of produced material was assessed using affinity HPLC and is summarized in FIG. 6 which clearly indicates that the setup that produced the highest yield was the XdevK strain in combination with KTXHIS-PelbLC-PelbHC.

Quality of the batch purified material was assessed with SCX-HPLC and is summarized in table 1. The material analyzed from the setup with the XdevK strain in combination with the expression vector based on the pRha67A plasmid is not reliable since this setups produces so little material that it is difficult to analyze. The material from the setup with XdevK strain in combination with the expression vector based on the pRha109A plasmid was harvested after a shorter induction time since the cells grew very slow as compared to the other cells. The SCX HPLC data summarized in table 1 clearly shows that the quality of the material produced in and purified from the XdevK strain in combination with KTXHIS-PelbLC-PelbHC is of superior purity (i.e. quality) as compared to the other setups.

TABLE 1

Summary of SCX HPLC purity data.

| Description | MG1655/ 67A | XdevK/ 109A | XdevK/ 67A | XdevK/ 67K | XdevK/ KTXHIS- PelbLC- PelbHC | XB201/ 67A |
|---|---|---|---|---|---|---|
| Ranibizumab purity in % | 30.6 | 53.0 | 59.3 | 73.8 | 83.0 | 71.5 |

Hence, in conclusion, the XdevK strain in combination with KTXHIS-PelbLC-PelbHC is superior compared to the other setups both in the quality of the produced ranibizumab and the yield of the produced ranibizumab.

Example 8—Comparative Experiments Showing Superior Control of Expression

Experimental Setup for Assessing Control of Expression

The expression vectors comprising the heavy and light chains of ranibizumab were transformed into XdevK and MG1655 using standard protocols. Overnight cultures were prepared by inoculating a single colony in 3 ml of LB-veg liquid media containing 100 μg/ml ampicillin or 50 μg/ml kanamycin depending on the plasmid used. Cultures were incubated in a 15 ml falcon tube at 37° C. with shaking for 16 hours. Cultures were then back-diluted (1:50) into 5 ml of LB-veg plus antibiotics in a 24-well growth plate, and incubated as before until an OD600 of approximately 0.3-0.5 was reached and different expression conditions were analyzed. One set of the cultures was grown in the presence of 0.2% glucose. Expression was induced by addition of 250 μM rhamnose in a subset of the cultures and incubated at 30° C. with shaking. A volume of cells corresponding to an OD600 of 0.2 units was collected (spun down) after 24 hours, resuspended in 20 μl 2× Laemlli loading buffer, boiled for 5 mins and analyzed (7.5 μl) by 12% mini SDS-PAGE. The gel was then immediately transferred to a nitrocellulose/PVDF membrane and probed using anti-Fab antibody.

Results and Discussion for Control of Expression

Figure 7A:
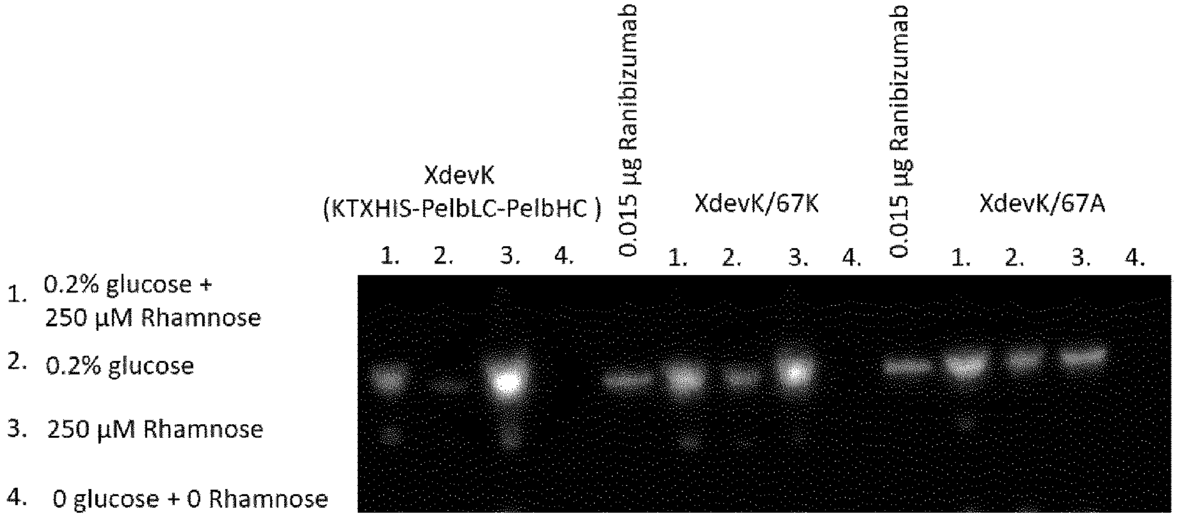
FIGS. 7*a*-7*c*—Western blots using anti-FAB antibody—Control of expression comparison in small scale experiment.
Figure 7B:
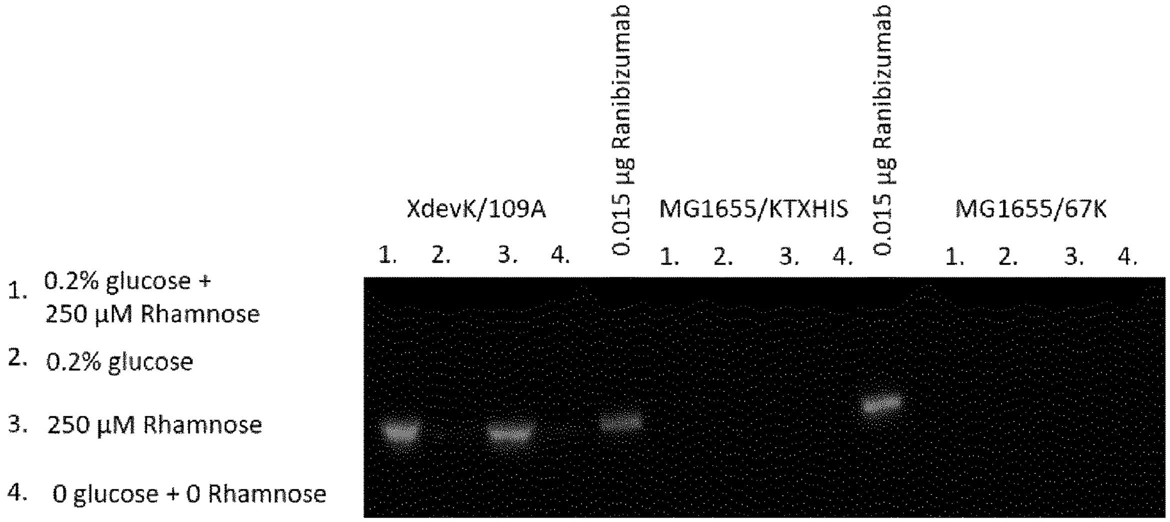
Figure 7C:
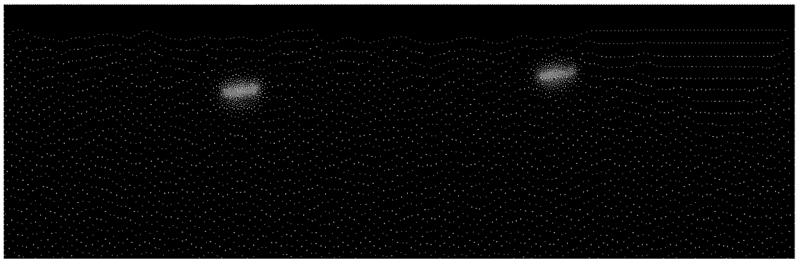

FIGS. 7*a*, 7*b* and 7*c* show the Western blots for the comparison of expression control. Each of the control lanes is loaded with ranibizumab. Samples in lane 1 from each setup were grown in the presence of 0.2% glucose and induced with 250 μm rhamnose. Samples in lane 2 from each setup were grown in the presence of 0.2% glucose. Samples in lane 3 from each setup were induced with 250 μm rhamnose. Samples in lane 4 from each setup were grown without any additions.

FIG. 7*a* shows:

- the accumulation of expressed ranibizumab in strain XdevK in combination with KTXHIS-PelbLC-PelbHC; and
- the accumulation of expressed ranibizumab in strain XdevK in combination with the expression vector based on the pRha67K (67K) plasmid; and
- the accumulation of expressed ranibizumab in strain XdevK in combination with the expression vector based on the pRha67A (67A) plasmid.

FIG. 7*b* shows:

- the accumulation of expressed ranibizumab in strain XdevK in combination with the expression vector based on the pRha109A (109A) plasmid;
- the accumulation of expressed ranibizumab in strain MG1655 in combination with KTXHIS-PelbLC-PelbHC;
- the accumulation of expressed ranibizumab in strain MG1655 in combination with the expression vector based on the pRha67K (67K) plasmid.

FIG. 7*c* shows:

- the accumulation of expressed ranibizumab in strain MG1655 in combination with the expression vector based on the pRha67A (67A) plasmid; and
- the accumulation of expressed ranibizumab in strain MG1655 in combination with the expression vector based on the pRha109A (109A) plasmid.

When the accumulation of ranibizumab is compared between the different setup in FIGS. 7*a*-7*c*, it is clear that highest expression of ranibizumab, induced by the addition of 250 μM rhamnose as indicated in lanes 3, was detected in XdevK strain in combination with KTXHIS-PelbLC-PelbHC.

Interestingly, as indicated in lanes 3 in FIGS. 7*b* and 7*c*, none of the setups involving the MG1655 strain resulted in visible expression of ranibizumab.

Moreover, of the setups that resulted in the expression of ranibizumab in lanes 3 (i.e. the setups in which the XdevK strain was used), the XdevK strain in combination with KTXHIS-PelbLC-PelbHC resulted in the lowest expression of ranibizumab when grown in the presence of 0.2% glucose as indicated in lanes 2. This suggest that the XdevK strain in combination with KTXHIS-PelbLC-PelbHC is less prone to leaky expression in the absence of inducer. Leaky expression can have a negative effect on growth of the cells leading to lower overall yield. Leaky expression can also affect the quality of the produced material leading to a mixture of different species of the accumulated expressed protein that can be problematic to handle in a downstream purification step and therefore lead to a lower yield and a complicate purification process Hence, the control of ranibizumab expression in the XdevK strain in combination with KTXHIS-PelbLC-PelbHC is superior when compared to the other setups.

In conclusion, the experimental results shown in Examples 4, 6, 7 and 8 demonstrate that the present invention provides the following advantageous and unexpected effects when compared with prior art expression vectors and/or host cells and therefore in particular is suitable for the industrial production of recombinant proteins

- superior titratability (example 6);
- superior purity and quality (example 7);
- superior titer (examples 4, 7 and 8); and
- superior control of expression (example 8).

REFERENCES

1. Holcroft C C et al. Interdependence of activation at rhaSR by cyclic AMP receptor protein, the RNA polymerase alpha subunit C-terminal domain, and rhaR. J Bacteriol. 2000; 182(23): 6774-6782
2. Hjelm, A. et al. Tailoring *Escherichia coli* for the 1-Rhamnose PBAD Promoter-Based Production of Membrane and Secretory Proteins. ACS synthetic biology 2017; 6 6: 985-994.
3. Wilms, B. et al. High-cell-density fermentation for production of L-N-carbamoylase using an expression system based on the *Escherichia coli* rhaBAD promoter. Biotechnol. Bioeng. 2001; 73: 95-103
4. Kumar, D. et al. QbD Based Media Development for the Production of Fab Fragments in *E. coli*. Bioengineering 2019; 6, 29.
5. Giacalone M J et al. "Toxic protein expression in *Escherichia coli* using a rhamnose-based tightly regulated and tunable promoter system. Biotechniques. 2006; 40(3): 355-364.
6. Choi, J. H. et al. Secretory and extracellular production of recombinant proteins using *Escherichia coli*. Appl Microbiol Biotechnol 2004; 64, 625-635

The invention claimed is:

1. A DNA construct for expressing ranibizumab in a bacterial host cell, wherein said DNA construct comprises:

a nucleotide sequence encoding ranibizumab, wherein the nucleotide sequence comprises (i) a nucleotide sequence encoding a light chain comprising the amino acid sequence of SEQ ID NO: 3, and (ii) a nucleotide sequence encoding a heavy chain comprising the amino acid sequence of SEQ ID NO: 4;

at least one nucleotide sequence encoding a signal peptide which is operably linked in the direction of transcription to the nucleotide sequence encoding the light chain and/or the nucleotide sequence encoding the heavy chain; and wherein said DNA construct further comprises nucleotide sequences encoding:

an rhaBAD promoter, an RhaR transcription activator, an RhaS transcription activator, an antibiotic resistance marker, a promoter operably linked to the nucleotide sequence encoding the antibiotic resistance marker an rrnB T1 terminator an rrnB T2 terminator, and a pMB1 origin of replication.

2. The DNA construct according to claim 1, wherein the antibiotic resistance marker is a kanamycin resistance marker;

the promoter operably linked to the nucleotide sequence encoding the antibiotic resistance marker is an AmpR promoter;

the rrnB T1 terminator comprises a nucleotide sequence with at least 90% sequence identity to the nucleotide sequence of SEQ ID NO:14;

the rrnB T2 terminator comprises a nucleotide sequence with at least 90% sequence identity to the nucleotide sequence of SEQ ID 15; and/or the pMB1 origin of replication comprises a nucleotide sequence with at least 90% sequence identity to the nucleotide sequence of SEQ ID 16.

3. The DNA construct according to claim 1, wherein the antibiotic resistance marker is a kanamycin resistance marker comprising the nucleotide sequence of SEQ ID 12;

the promoter operably linked to the nucleotide sequence encoding the antibiotic resistance marker is an AmpR promoter comprising the nucleotide sequence of SEQ ID 13;

the rrnB T1 terminator comprises the nucleotide sequence of SEQ ID 14;

the rrnB T2 terminator comprises the nucleotide sequence of SEQ ID 15; and/or the pMB1 origin of replication comprises the nucleotide sequence of SEQ ID 16.

4. The DNA construct according to claim 1, wherein:

the rhaBAD promoter comprises a nucleotide sequence with at least 90% sequence identity to the nucleotide sequence of SEQ ID NO: 8;

the RhaR transcription activator comprises a nucleotide sequence with at least 90% sequence identity to the nucleotide sequence of SEQ ID NO: 9;

the RhaS transcription activator comprises a sequence with at least 90% sequence identity to the nucleotide sequence of SEQ ID NO: 11;

the antibiotic resistance marker is a kanamycin resistance marker comprising a sequence with at least 90% sequence identity to the nucleotide sequence of SEQ ID NO: 12;

the Promoter operably linked to the nucleotide sequence encoding the antibiotic resistance marker is an AmpR promoter comprising a sequence with at least 90% sequence identity to the nucleotide sequence of SEQ ID NO: 13;

the rrnB T1 terminator comprises a sequence with at least 90% sequence identity to the nucleotide sequence of SEQ ID NO: 14;

the rrnB T2 terminator comprises a sequence with at least 90% sequence identity to the nucleotide sequence of SEQ ID NO: 15; and the pMB1 origin of replication comprises a sequence with at least 90% sequence identity to the nucleotide sequence of SEQ ID NO: 16.

5. The DNA construct according to claim 1, wherein the nucleotide sequence encoding ranibizumab is operably linked to the rhaBAD promoter.

6. The DNA construct according to claim 1, wherein (i) the nucleotide sequence encoding the light chain comprises a sequence with at least 90% sequence identity to the nucleotide sequence of SEQ ID NO:5, and/or (ii) the nucleotide sequence encoding the heavy chain comprises a sequence with at least 90% sequence identity the nucleotide sequence of SEQ ID NO:6.

7. The DNA construct according to claim 1, wherein (i) the nucleotide sequence encoding the light chain comprises the sequence of SEQ ID NO: 5, and/or (ii) the nucleotide sequence encoding the heavy chain comprises the sequence of SEQ ID NO: 6.

8. The DNA construct according to claim 7, wherein the nucleotide sequence encoding the signal peptide is operably linked in the direction of transcription to both of nucleotide sequences of SEQ ID NO: 5 and SEQ ID NO: 6.

9. The DNA construct according to claim 1, wherein the signal peptide is PelB.

10. The DNA construct according to claim 9, wherein the nucleotide sequence encoding the PelB signal peptide comprises a sequence with at least 90% sequence identity to the nucleotide sequence of SEQ ID NO: 7.

11. The DNA construct according to claim 9, wherein said DNA construct comprises a sequence with at least 90% sequence identity to the nucleotide sequence of SEQ ID NO: 17.

12. An expression vector comprising the DNA construct according to claim 1.

13. A bacterial host cell comprising the DNA construct according to claim 1.

14. A host cell according to claim 13, wherein said host cell either comprises (i) a chromosome which comprises a mutation in the nucleotide sequence of the rhaB gene which renders RhaB inactive, or (ii) a chromosome in which the nucleotide sequence encoding RhaB is deleted.

15. A host cell according to claim 13, wherein said host cell is an *Escherichia coli* W3110 cell.

16. A host cell according to claim 13, wherein said host cell is an *Escherichia coli* W3110 cell comprising a chromosome which comprises a sequence with at least 90% sequence identity to the nucleotide sequence of SEQ ID 2.

17. A method of producing ranibizumab comprising the step of exposing the bacterial host cell according to claim 13 to rhamnose, thereby inducing expression of ranibizumab.

18. A method according to claim 17, further comprising the step of recovering ranibizumab from the bacterial host cell.

19. The DNA construct according to claim 2, wherein the nucleotide sequence encoding the kanamycin resistance marker comprises a nucleotide sequence with at least 90% sequence identity to the nucleotide sequence of SEQ ID NO: 12; and/or the nucleotide sequence encoding the AmpR promoter comprises a nucleotide sequence with a least 90% sequence identity to the nucleotide sequence of SEQ ID NO:13.

20. The DNA construct according to claim 19, wherein the nucleotide sequence encoding the kanamycin resistance marker comprises the nucleotide sequence of SEQ ID NO: 12; and/or the nucleotide sequence encoding the AmpR promoter comprises the nucleotide sequence of SEQ ID NO:13.

21. The DNA construct according to claim 2, wherein the nucleotide sequence encoding the rrnB T1 terminator comprises the nucleotide sequence of SEQ ID 14;

the nucleotide sequence encoding the rrnB T2 terminator comprises the nucleotide sequence of SEQ ID 15; and/or the nucleotide sequence encoding the pMB1 origin of replication comprises the nucleotide sequence of SEQ ID 16.

22. A bacterial host cell comprising the expression vector according to claim 12.

23. The bacterial host cell according to claim 13, wherein said bacterial host cell is an *Escherichia coli* cell.

24. The bacterial host cell according to claim 23, wherein said *Escherichia coli* cell is an *E. coli* K-12 cell.

25. The host cell according to claim 15, wherein the host cell comprises a chromosome which comprises a frame shift-mutation in the nucleotide sequence encoding RhaB.

26. The host cell according to claim 16, wherein the chromosome of the host cell further comprises a nucleotide sequence encoding RhaT.

27. The method according to claim 18, further comprising one or more step(s) of purifying the recovered ranibizumab.

28. The method according to claim 27, wherein said one or more step(s) of purifying the recovered ranibizumab comprise one or more chromatography steps.

* * * * *

SEQUENCE LISTING

<160> NUMBER OF SEQ ID NOS: 21

<210> SEQ ID NO 1
<211> LENGTH: 4673
<212> TYPE: DNA
<213> ORGANISM: Artificial Sequence
<220> FEATURE:
<223> OTHER INFORMATION: KTXHIS

<400> SEQUENCE: 1
atctttctgc gaattgagat gacgccactg gctgggcgtc atcccggttt cccgggtaaa 60
caccaccgaa aaatagttac tatcttcaaa gccacattcg gtcgaaatat cactgattaa 120
caggcggcta tgctggagaa gatattgcgc atgacacact ctgacctgtc gcagatattg 180
attgatggtc attccagtct gctggcgaaa ttgctgacgc aaaacgcgct cactgcacga 240
tgcctcatca caaaatttat ccagcgcaaa gggacttttc aggctagccg ccagccgggt 300
aatcagctta tccagcaacg tttcgctgga tgttggcggc aacgaatcac tggtgtaacg 360
atggcgattc agcaacatca ccaactgccc gaacagcaac tcagccattt cgttagcaaa 420
cggcacatgc tgactacttt catgctcaag ctgaccaata acctgccgcg cctgcgccat 480
ccccatgcta cctaagcgcc agtgtggttg ccctgcgctg gcgttaaatc ccggaatcgc 540
cccctgccag tcaagattca gcttcagacg ctccgggcaa taaataatat tctgcaaaac 600
cagatcgtta acggaagcgt aggagtgttt atcatcagca tgaatgtaaa agagatcgcc 660
acgggtaatg cgataagggc gatcgttgag tacatgcagg ccattaccgc gccagacaat 720

```
caccagctca caaaaatcat gtgtatgttc agcaaagaca tcttgcggat aacggtcagc    780
cacagcgact gcctgctggt cgctggcaaa aaaatcatct ttgagaagtt ttaactgatg    840
cgccaccgtg gctacctcgg ccagagaacg aagttgatta ttcgcaatat ggcgtacaaa    900
tacgttgaga agattcgcgt tattgcagaa agccatcccg tccctggcga atatcacgcg    960
gtgaccagtt aaactctcgg cgaaaaagcg tcgaaaagtg gttactgtcg ctgaatccac   1020
agcgataggc gatgtcagta acgctggcct cgctgtggcg tagcagatgt cgggctttca   1080
tcagtcgcag gcggttcagg tatcgctgag gcgtcagtcc cgtttgctgc ttaagctgcc   1140
gatgtagcgt acgcagtgaa agagaaaatt gatccgccac ggcatcccaa ttcacctcat   1200
cggcaaaatg gtcctccagc caggccagaa gcaagttgag acgtgatgcg ctgttttcca   1260
ggttctcctg caaactgctt ttacgcagca agagcagtaa ttgcataaac aagatctcgc   1320
gactggcggt cgagggtaaa tcattttccc cttcctgctg ttccatctgt gcaaccagct   1380
gtcgcacctg ctgcaatacg ctgtggttaa cgcgccagtg agacggatac tgcccatcca   1440
gctcttgtgg cagcaactga ttcagcccgg cgagaaactg aaatcgatcc ggcgagcgat   1500
acagcacatt ggtcagacac agattatcgg tatgttcata cagatgccga tcatgatcgc   1560
gtacgaaaca gaccgtgcca ccggtgatgg tatagggctg cccattaaac acatgaatac   1620
ccgtgccatg ttcgacaatc acaatttcat gaaaatcatg atgatgttca ggaaaatccg   1680
cctgcgggag ccggggttct atcgccacgg acgcgttacc agacggaaaa aaatccacac   1740
tatgtaatac ggtcatactg gcctcctgat gtcgtcaaca cggcgaaata gtaatcacga   1800
ggtcaggttc ttaccttaaa ttttcgacgg aaaaccacgt aaaaaacgtc gatttttcaa   1860
gatacagcgt gaattttcag gaaatgcggt gagcatcaca tcaccacaat tcagcaaatt   1920
gtgaacatca tcacgttcat ctttccctgg ttgccaatgg cccattttct tgtcagtaac   1980
gagaaggtcg cgaatccagg cgctttttag actggtcgta atgaaattca ggaggaattc   2040
catatggcgg ccgcactcga gcaccaccac caccaccact gatgaagacg gccgcctagg   2100
ggtaccgagc tcggatcctc tagagtcgac ctgcaggcat gcaagcttgg ctgttttggc   2160
ggatgagaga agattttcag cctgatacag attaaatcag aacgcagaag cggtctgata   2220
aaacagaatt tgcctggcgg cagtagcgcg gtggtcccac ctgaccccat gccgaactca   2280
gaagtgaaac gccgtagcgc cgatggtagt gtggggtctc cccatgcgag agtagggaac   2340
tgccaggcat caaataaaac gaaaggctca gtcgaaagac tgggcctttc gttttatctg   2400
ttgtttgtcg gtgaacgctc tcctgagtag gacaaatccg ccgggagcgg atttgaacgt   2460
tgcgaagcaa cggcccggag ggtggcgggc aggacgcccg ccataaactg ccaggcatca   2520
aattaagcag aaggccatcc tgacggatgg cctttttgcg tttctacaaa ctcttttgtt   2580
tatttttcta aatacattca aatatgtatc cgctcatgag actaggcttc cgcgccctca   2640
tccgaaaggg cgtattcata tatgcggtgt gaaataccgc acagatgcgt aaggagaaaa   2700
taccgcatca ggcgctcttc cgcttcctcg ctcactgact cgctgcgctc ggtcgttcgg   2760
ctgcggcgag cggtatcagc tcactcaaag gcggtaatac ggttatccac agaatcaggg   2820
gataacgcag gaaagaacat gtgagcaaaa ggccagcaaa aggccaggaa ccgtaaaaag   2880
gccgcgttgc tggcgttttt ccataggctc cgcccccctg acgagcatca caaaaatcga   2940
cgctcaagtc agaggtggcg aaacccgaca ggactataaa gataccaggc gtttccccct   3000
ggaagctccc tcgtgcgctc tcctgttccg accctgccgc ttaccggata cctgtccgcc   3060
```

tttctccctt cgggaagcgt ggcgctttct catagctcac gctgtaggta tctcagttcg 3120
gtgtaggtcg ttcgctccaa gctgggctgt gtgcacgaac cccccgttca gcccgaccgc 3180
tgcgccttat ccggtaacta tcgtcttgag tccaacccgg taagacacga cttatcgcca 3240
ctggcagcag ccactggtaa caggattagc agagcgaggt atgtaggcgg tgctacagag 3300
ttcttgaagt ggtggcctaa ctacggctac actagaagga cagtatttgg tatctgcgct 3360
ctgctgaagc cagttacctt cggaaaaaga gttggtagct cttgatccgg caaacaaacc 3420
accgctggta gcggtggttt ttttgtttgc aagcagcaga ttacgcgcag aaaaaaagga 3480
tctcaagaag atcctttgat cttttctacg gggtctgacg ctcagtggaa cgaaaactca 3540
cgttaaggga ttttggtcat gagattatca aaaaggatct tcacctagat ccttttaaat 3600
taaaaatgaa gttttaaatc aatctaaagt atatatgagt aaacttggtc tgacagttag 3660
aaaaactcat cgagcatcaa atgaaactgc aatttattca tatcaggatt atcaatacca 3720
tatttttgaa aaagccgttt ctgtaatgaa ggagaaaact caccgaggca gttccatagg 3780
atggcaagat cctggtatcg gtctgcgatt ccgactcgtc caacatcaat acaacctatt 3840
aatttcccct cgtcaaaaat aaggttatca agtgagaaat caccatgagt gacgactgaa 3900
tccggtgaga atggcaaaag tttatgcatt tctttccaga cttgttcaac aggccagcca 3960
ttacgctcgt catcaaaatc actcgcatca accaaaccgt tattcattcg tgattgcgcc 4020
tgagcgagac gaaatacgcg atcgctgtta aaaggacaat tacaaacagg aatcgaatgc 4080
aaccggcgca ggaacactgc cagcgcatca acaatatttt cacctgaatc aggatattct 4140
tctaatacct ggaatgctgt tttcccgggg atcgcagtgg tgagtaacca tgcatcatca 4200
ggagtacgga taaaatgctt gatggtcgga agaggcataa attccgtcag ccagtttagt 4260
ctgaccatct catctgtaac atcattggca acgctacctt tgccatgttt cagaaacaac 4320
tctggcgcat cgggcttccc atacaatcga tagattgtcg cacctgattg cccgacatta 4380
tcgcgagccc atttataccc atataaatca gcatccatgt tggaatttaa tcgcggccta 4440
gagcaagacg tttcccgttg aatatggctc atactcttcc tttttcaata ttattgaagc 4500
atttatcagg gttattgtct catgagcgga tacatatttg aatgtattta gaaaaataaa 4560
caaatagggg ttccgcgcac atttccccga aaagtgccac ctgacgtcta agaaaccatt 4620
attatcatga cattaaccta taaaaatagg cgtatcacga ggccctttcg tct 4673

<210> SEQ ID NO 2
<211> LENGTH: 767
<212> TYPE: DNA
<213> ORGANISM: Artificial Sequence
<220> FEATURE:
<223> OTHER INFORMATION: frame shift mutation

<400> SEQUENCE: 2
gttggccccg ctccacgcca gtagcgactc gtcccagtcg tcgctattga tattgaccag 60
ttgcgtggtc gtggcgttgg tatattccca gttcatcttg ccggtcaggc gataactgaa 120
gtaatccggc atcagcagag cgtgagcaat gtgtggaata agttcaggtt gttgctccgt 180
cagcgcacgc aactgataaa gcgtattgaa gggcagaaac tggatgccgc tacgttgata 240
aatatcgcgt ttgccgagtt gttgttgtgc ctgcgccatt aggccattgg tgcggctatc 300
gcgataagca acgggcaggc ccacacgctg accctgttgg tcgagcagca caaagtccac 360
gccccaggta tcaatcccaa tgctatcgcg atacgaatcc cttcctcgca caccttgttt 420
aatccaaggc gaatggcact ttccaggcta tccacatccc aggtgacata gccgttctga 480

```
ctatgcagcc cattgttaaa acgatggatt tcgcgcagcg tcaggctgcg gcattcacgc    540

tcgtaacgcg ccagcatcac gcgcccactg gatgcgccga gatcgacggc gacacaattg    600

cgaaaggtca taatgtgatc ctgctgaatt tcattacgac cagtctaaaa agcgcctgaa    660

ttcgcgacct tctcgttact gacaggaaaa tgggccattg gcaaccaggg aaagatgaac    720

gtgatgatgt tcacaatttg ctgaattgtg gtgatgtgat gctcacc                  767


<210> SEQ ID NO 3
<211> LENGTH: 214
<212> TYPE: PRT
<213> ORGANISM: Artificial Sequence
<220> FEATURE:
<223> OTHER INFORMATION: Ranibizumab light chain

<400> SEQUENCE: 3

Asp Ile Gln Leu Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Val Leu Ile
        35                  40                  45

Tyr Phe Thr Ser Ser Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Val Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 4
<211> LENGTH: 231
<212> TYPE: PRT
<213> ORGANISM: Artificial Sequence
<220> FEATURE:
<223> OTHER INFORMATION: Ranibizumab heavy chain

<400> SEQUENCE: 4

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Asp Phe Thr His Tyr
            20                  25                  30
```

-continued

```
Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro Tyr Tyr Tyr Gly Thr Ser His Trp Tyr Phe Asp Val
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Leu
225                 230
```

<210> SEQ ID NO 5
<211> LENGTH: 645
<212> TYPE: DNA
<213> ORGANISM: Artificial Sequence
<220> FEATURE:
<223> OTHER INFORMATION: ranibizumab light chain

<400> SEQUENCE: 5

```
gatattcagc tgacccagag cccgagcagc ctgagcgcaa gcgttggtga tcgtgttacc     60

attacctgta gcgcaagcca ggatattagc aattatctga attggtatca gcagaaaccg    120

ggtaaagcac cgaaagtgct gatctatttt accagcagcc tgcatagcgg tgttccgagc    180

cgttttagcg gtagcggtag tggcaccgat tttaccctga ccattagcag cctgcagccg    240

gaagattttg caacctatta ttgtcagcag tatagcaccg ttccgtggac ctttggtcag    300

ggcaccaaag ttgaaattaa acgtaccgtt gcagcaccga gcgtttttat ctttccgcct    360

agtgatgaac agctgaaaag cggcaccgca agcgttgttt gtctgctgaa taacttttat    420

ccgcgtgaag caaaagttca gtggaaagtt gataatgcac tgcagagcgg taatagccaa    480

gaaagcgtta ccgaacagga tagcaaagat agcacctata gcctgagcag caccctgacc    540

ctgagcaaag cagattatga aaaacacaaa gtgtatgcct gcgaagttac ccatcagggt    600

ctgagcagtc cggttaccaa aagttttaat cgtggtgaat gctaa                    645
```

<210> SEQ ID NO 6
<211> LENGTH: 696
<212> TYPE: DNA
<213> ORGANISM: Artificial Sequence
<220> FEATURE:
<223> OTHER INFORMATION: ranibizumab heavy chain

<400> SEQUENCE: 6
gaagttcagc tggttgaaag cggtggtggt ctggttcagc ctggtggtag cctgcgtctg 60
agctgtgcag caagcggtta tgattttacc cattatggta tgaattgggt tcgtcaggca 120
ccgggtaaag gtctggaatg ggttggttgg attaatacct ataccggtga accgacctat 180
gcagcagatt ttaaacgtcg ttttaccttt agcctggata ccagcaaaag caccgcatat 240
ctgcagatga atagcctgcg tgcagaggat accgcagtgt attattgtgc aaaatatccg 300
tattattacg gcaccagcca ttggtatttc gatgtttggg gtcagggcac cctggttacc 360
gttagcagcg caagcaccaa aggtccgagc gtttttccgc tggcaccgag cagcaaaagt 420
accagcggtg gcaccgcagc actgggttgt ctggttaaag attattttcc ggaaccggtt 480
accgtgagct ggaatagcgg tgcactgacc agcggtgttc atacctttcc ggcagttctg 540
cagagcagcg gtctgtatag cctgagcagc gttgttaccg ttccgagcag cagcctgggc 600
acccagacct atatttgtaa tgttaatcat aaaccgagca ataccaaagt ggataaaaaa 660
gtggaaccga aaagctgcga taaaacccat ctgtaa 696

<210> SEQ ID NO 7
<211> LENGTH: 66
<212> TYPE: DNA
<213> ORGANISM: Artificial Sequence
<220> FEATURE:
<223> OTHER INFORMATION: PelB signal peptide - DNA

<400> SEQUENCE: 7
atgaaatatc tgctgccgac cgcagcagcg ggtctgctgc tgctggcagc acagcctgca 60
atggca 66

<210> SEQ ID NO 8
<211> LENGTH: 119
<212> TYPE: DNA
<213> ORGANISM: Artificial Sequence
<220> FEATURE:
<223> OTHER INFORMATION: rhaBAD promoter

<400> SEQUENCE: 8
caccacaatt cagcaaattg tgaacatcat cacgttcatc tttccctggt tgccaatggc 60
ccattttctt gtcagtaacg agaaggtcgc gaatccaggc gctttttaga ctggtcgta 119

<210> SEQ ID NO 9
<211> LENGTH: 936
<212> TYPE: DNA
<213> ORGANISM: Artificial Sequence
<220> FEATURE:
<223> OTHER INFORMATION: RhaR transcription activator

<400> SEQUENCE: 9
atggctttct gcaataacgc gaatcttctc aacgtatttg tacgccatat tgcgaataat 60
caacttcgtt ctctggccga ggtagccacg gtggcgcatc agttaaaact tctcaaagat 120
gatttttttg ccagcgacca gcaggcagtc gctgtggctg accgttatcc gcaagatgtc 180
tttgctgaac atacacatga tttttgtgag ctggtgattg tctggcgcgg taatggcctg 240
catgtactca acgatcgccc ttatcgcatt acccgtggcg atctctttta cattcatgct 300
gatgataaac actcctacgc ttccgttaac gatctggttt tgcagaatat tatttattgc 360
ccggagcgtc tgaagctgaa tcttgactgg caggggggcga ttccgggatt taacgccagc 420
gcagggcaac cacactggcg cttaggtagc atggggatgg cgcaggcgcg gcaggttatt 480
ggtcagcttg agcatgaaag tagtcagcat gtgccgtttg ctaacgaaat ggctgagttg 540
ctgttcgggc agttggtgat gttgctgaat cgccatcgtt acaccagtga ttcgttgccg 600
ccaacatcca gcgaaacgtt gctggataag ctgattaccc ggctggcggc tagcctgaaa 660
agtccctttg cgctggataa attttgtgat gaggcatcgt gcagtgagcg cgttttgcgt 720
cagcaatttc gccagcagac tggaatgacc atcaatcaat atctgcgaca ggtcagagtg 780
tgtcatgcgc aatatcttct ccagcatagc cgcctgttaa tcagtgatat ttcgaccgaa 840
tgtggctttg aagatagtaa ctatttttcg gtggtgttta cccgggaaac cgggatgacg 900
cccagccagt ggcgtcatct caattcgcag aaagat 936

<210> SEQ ID NO 10
<211> LENGTH: 36
<212> TYPE: DNA
<213> ORGANISM: Artificial Sequence
<220> FEATURE:
<223> OTHER INFORMATION: RhaR extended

<400> SEQUENCE: 10
agacgaaagg gcctcgtgat acgcctattt ttatag 36

<210> SEQ ID NO 11
<211> LENGTH: 837
<212> TYPE: DNA
<213> ORGANISM: Artificial Sequence
<220> FEATURE:
<223> OTHER INFORMATION: RhaS transcription activator

<400> SEQUENCE: 11
atgaccgtat tacatagtgt ggattttttt ccgtctggta acgcgtccgt ggcgatagaa 60
ccccggctcc cgcaggcgga ttttcctgaa catcatcatg attttcatga aattgtgatt 120
gtcgaacatg gcacgggtat tcatgtgttt aatgggcagc cctataccat caccggtggc 180
acggtctgtt tcgtacgcga tcatgatcgg catctgtatg aacataccga taatctgtgt 240
ctgaccaatg tgctgtatcg ctcgccggat cgatttcagt ttctcgccgg gctgaatcag 300
ttgctgccac aagagctgga tgggcagtat ccgtctcact ggcgcgttaa ccacagcgta 360
ttgcagcagg tgcgacagct ggttgcacag atggaacagc aggaagggga aaatgattta 420
ccctcgaccg ccagtcgcga gatcttgttt atgcaattac tgctcttgct gcgtaaaagc 480
agtttgcagg agaacctgga aaacagcgca tcacgtctca acttgcttct ggcctggctg 540
gaggaccatt ttgccgatga ggtgaattgg gatgccgtgg cggatcaatt ttctctttca 600
ctgcgtacgc tacatcggca gcttaagcag caaacgggac tgacgcctca gcgatacctg 660
aaccgcctgc gactgatgaa agcccgacat ctgctacgcc acagcgaggc cagcgttact 720
gacatcgcct atcgctgtgg attcagcgac agtaaccact tttcgacgct ttttcgccga 780
gagtttaact ggtcaccgcg tgatattcgc cagggacggg atggctttct gcaataa 837

<210> SEQ ID NO 12
<211> LENGTH: 816
<212> TYPE: DNA
<213> ORGANISM: Artificial Sequence
<220> FEATURE:
<223> OTHER INFORMATION: KanR

<400> SEQUENCE: 12
atgagccata ttcaacggga aacgtcttgc tctaggccgc gattaaattc caacatggat 60
gctgatttat atgggtataa atgggctcgc gataatgtcg ggcaatcagg tgcgacaatc 120
tatcgattgt atgggaagcc cgatgcgcca gagttgtttc tgaaacatgg caaaggtagc 180
gttgccaatg atgttacaga tgagatggtc agactaaact ggctgacgga atttatgcct 240
cttccgacca tcaagcattt tatccgtact cctgatgatg catggttact caccactgcg 300
atccccggga aaacagcatt ccaggtatta gaagaatatc ctgattcagg tgaaaatatt 360
gttgatgcgc tggcagtgtt cctgcgccgg ttgcattcga ttcctgtttg taattgtcct 420
tttaacagcg atcgcgtatt tcgtctcgct caggcgcaat cacgaatgaa taacggtttg 480
gttgatgcga gtgattttga tgacgagcgt aatggctggc ctgttgaaca agtctggaaa 540
gaaatgcata aacttttgcc attctcaccg gattcagtcg tcactcatgg tgatttctca 600
cttgataacc ttatttttga cgaggggaaa ttaataggtt gtattgatgt tggacgagtc 660
ggaatcgcag accgatacca ggatcttgcc atcctatgga actgcctcgg tgagttttct 720
ccttcattac agaaacggct ttttcaaaaa tatggtattg ataatcctga tatgaataaa 780
ttgcagtttc atttgatgct cgatgagttt ttctaa 816

<210> SEQ ID NO 13
<211> LENGTH: 105
<212> TYPE: DNA
<213> ORGANISM: Artificial Sequence
<220> FEATURE:
<223> OTHER INFORMATION: AmpR promoter

<400> SEQUENCE: 13
cgcggaaccc ctatttgttt atttttctaa atacattcaa atatgtatcc gctcatgaga 60
caataaccct gataaatgct tcaataatat tgaaaaagga agagt 105

<210> SEQ ID NO 14
<211> LENGTH: 87
<212> TYPE: DNA
<213> ORGANISM: Artificial Sequence
<220> FEATURE:
<223> OTHER INFORMATION: rrnB T1 terminator

<400> SEQUENCE: 14
caaataaaac gaaaggctca gtcgaaagac tgggcctttc gttttatctg ttgtttgtcg 60
gtgaacgctc tcctgagtag gacaaat 87

<210> SEQ ID NO 15
<211> LENGTH: 28
<212> TYPE: DNA
<213> ORGANISM: Artificial Sequence
<220> FEATURE:
<223> OTHER INFORMATION: rrnB T2 terminator

<400> SEQUENCE: 15
agaaggccat cctgacggat ggcctttt 28

<210> SEQ ID NO 16
<211> LENGTH: 589
<212> TYPE: DNA
<213> ORGANISM: Artificial Sequence
<220> FEATURE:
<223> OTHER INFORMATION: pMB1 origin of replication

<400> SEQUENCE: 16
tttccatagg ctccgccccc ctgacgagca tcacaaaaat cgacgctcaa gtcagaggtg 60
gcgaaacccg acaggactat aaagatacca ggcgtttccc cctggaagct ccctcgtgcg 120

```
ctctcctgtt ccgaccctgc cgcttaccgg atacctgtcc gcctttctcc cttcgggaag    180

cgtggcgctt tctcatagct cacgctgtag gtatctcagt tcggtgtagg tcgttcgctc    240

caagctgggc tgtgtgcacg aaccccccgt tcagcccgac cgctgcgcct tatccggtaa    300

ctatcgtctt gagtccaacc cggtaagaca cgacttatcg ccactggcag cagccactgg    360

taacaggatt agcagagcga ggtatgtagg cggtgctaca gagttcttga agtggtggcc    420

taactacggc tacactagaa ggacagtatt tggtatctgc gctctgctga agccagttac    480

cttcggaaaa agagttggta gctcttgatc cggcaaacaa accaccgctg gtagcggtgg    540

tttttttgtt tgcaagcagc agattacgcg cagaaaaaaa ggatctcaa                589


<210> SEQ ID NO 17
<211> LENGTH: 6088
<212> TYPE: DNA
<213> ORGANISM: Artificial Sequence
<220> FEATURE:
<223> OTHER INFORMATION: KTXHIS-pelbLC-pelbHC

<400> SEQUENCE: 17

atctttctgc gaattgagat gacgccactg gctgggcgtc atcccggttt cccgggtaaa     60

caccaccgaa aaatagttac tatcttcaaa gccacattcg gtcgaaatat cactgattaa    120

caggcggcta tgctggagaa gatattgcgc atgacacact ctgacctgtc gcagatattg    180

attgatggtc attccagtct gctggcgaaa ttgctgacgc aaaacgcgct cactgcacga    240

tgcctcatca caaaatttat ccagcgcaaa gggacttttc aggctagccg ccagccgggt    300

aatcagctta tccagcaacg tttcgctgga tgttggcggc aacgaatcac tggtgtaacg    360

atggcgattc agcaacatca ccaactgccc gaacagcaac tcagccattt cgttagcaaa    420

cggcacatgc tgactacttt catgctcaag ctgaccaata acctgccgcg cctgcgccat    480

ccccatgcta cctaagcgcc agtgtggttg ccctgcgctg gcgttaaatc ccggaatcgc    540

cccctgccag tcaagattca gcttcagacg ctccgggcaa taaataatat tctgcaaaac    600

cagatcgtta acggaagcgt aggagtgttt atcatcagca tgaatgtaaa agagatcgcc    660

acgggtaatg cgataagggc gatcgttgag tacatgcagg ccattaccgc gccagacaat    720

caccagctca caaaaatcat gtgtatgttc agcaaagaca tcttgcggat aacggtcagc    780

cacagcgact gcctgctggt cgctggcaaa aaaatcatct ttgagaagtt ttaactgatg    840

cgccaccgtg gctacctcgg ccagagaacg aagttgatta ttcgcaatat ggcgtacaaa    900

tacgttgaga agattcgcgt tattgcagaa agccatcccg tccctggcga atatcacgcg    960

gtgaccagtt aaactctcgg cgaaaaagcg tcgaaaagtg gttactgtcg ctgaatccac   1020

agcgataggc gatgtcagta acgctggcct cgctgtggcg tagcagatgt cgggctttca   1080

tcagtcgcag gcggttcagg tatcgctgag gcgtcagtcc cgtttgctgc ttaagctgcc   1140

gatgtagcgt acgcagtgaa agagaaaatt gatccgccac ggcatcccaa ttcacctcat   1200

cggcaaaatg gtcctccagc caggccagaa gcaagttgag acgtgatgcg ctgttttcca   1260

ggttctcctg caaactgctt ttacgcagca agagcagtaa ttgcataaac aagatctcgc   1320

gactggcggt cgagggtaaa tcattttccc cttcctgctg ttccatctgt gcaaccagct   1380

gtcgcacctg ctgcaatacg ctgtggttaa cgcgccagtg agacggatac tgcccatcca   1440

gctcttgtgg cagcaactga ttcagcccgg cgagaaactg aaatcgatcc ggcgagcgat   1500

acagcacatt ggtcagacac agattatcgg tatgttcata cagatgccga tcatgatcgc   1560
```

gtacgaaaca gaccgtgcca ccggtgatgg tatagggctg cccattaaac acatgaatac 1620
ccgtgccatg ttcgacaatc acaatttcat gaaaatcatg atgatgttca ggaaaatccg 1680
cctgcgggag ccggggttct atcgccacgg acgcgttacc agacggaaaa aaatccacac 1740
tatgtaatac ggtcatactg gcctcctgat gtcgtcaaca cggcgaaata gtaatcacga 1800
ggtcaggttc ttaccttaaa ttttcgacgg aaaaccacgt aaaaaacgtc gatttttcaa 1860
gatacagcgt gaattttcag gaaatgcggt gagcatcaca tcaccacaat tcagcaaatt 1920
gtgaacatca tcacgttcat ctttccctgg ttgccaatgg cccattttct tgtcagtaac 1980
gagaaggtcg cgaatccagg cgctttttag actggtcgta atgaaattca ggaggaattc 2040
ctaatgaaat atctgctgcc gaccgcagca gcgggtctgc tgctgctggc agcacagcct 2100
gcaatggcag atattcagct gacccagagc ccgagcagcc tgagcgcaag cgttggtgat 2160
cgtgttacca ttacctgtag cgcaagccag gatattagca attatctgaa ttggtatcag 2220
cagaaaccgg gtaaagcacc gaaagtgctg atctatttta ccagcagcct gcatagcggt 2280
gttccgagcc gttttagcgg tagcggtagt ggcaccgatt ttaccctgac cattagcagc 2340
ctgcagccgg aagattttgc aacctattat tgtcagcagt atagcaccgt tccgtggacc 2400
tttggtcagg gcaccaaagt tgaaattaaa cgtaccgttg cagcaccgag cgtttttatc 2460
tttccgccta gtgatgaaca gctgaaaagc ggcaccgcaa gcgttgtttg tctgctgaat 2520
aacttttatc cgcgtgaagc aaaagttcag tggaaagttg ataatgcact gcagagcggt 2580
aatagccaag aaagcgttac cgaacaggat agcaaagata gcacctatag cctgagcagc 2640
accctgaccc tgagcaaagc agattatgaa aaacacaaag tgtatgcctg cgaagttacc 2700
catcagggtc tgagcagtcc ggttaccaaa agttttaatc gtggtgaatg ctaataatct 2760
agaactgtta tcgatatcag gaggattagc atatgaaata tctgctgccg accgcagcag 2820
cgggtctgct gctgctggca gcacagcctg caatggcaga agttcagctg gttgaaagcg 2880
gtggtggtct ggttcagcct ggtggtagcc tgcgtctgag ctgtgcagca agcggttatg 2940
attttaccca ttatggtatg aattgggttc gtcaggcacc gggtaaaggt ctggaatggg 3000
ttggttggat taatacctat accggtgaac cgacctatgc agcagatttt aaacgtcgtt 3060
ttacctttag cctggatacc agcaaaagca ccgcatatct gcagatgaat agcctgcgtg 3120
cagaggatac cgcagtgtat tattgtgcaa aatatccgta ttattacggc accagccatt 3180
ggtatttcga tgtttggggt cagggcaccc tggttaccgt tagcagcgca agcaccaaag 3240
gtccgagcgt tttttccgctg gcaccgagca gcaaaagtac cagcggtggc accgcagcac 3300
tgggttgtct ggttaaagat tattttccgg aaccggttac cgtgagctgg aatagcggtg 3360
cactgaccag cggtgttcat acctttccgg cagttctgca gagcagcggt ctgtatagcc 3420
tgagcagcgt tgttaccgtt ccgagcagca gcctgggcac ccagacctat atttgtaatg 3480
ttaatcataa accgagcaat accaaagtgg ataaaaaagt ggaaccgaaa agctgcgata 3540
aaacccatct gtaataaaag cttggctgtt ttggcggatg agagaagatt ttcagcctga 3600
tacagattaa atcagaacgc agaagcggtc tgataaaaca gaatttgcct ggcggcagta 3660
gcgcggtggt cccacctgac cccatgccga actcagaagt gaaacgccgt agcgccgatg 3720
gtagtgtggg gtctccccat gcgagagtag ggaactgcca ggcatcaaat aaaacgaaag 3780
gctcagtcga aagactgggc ctttcgtttt atctgttgtt tgtcggtgaa cgctctcctg 3840
agtaggacaa atccgccggg agcggatttg aacgttgcga agcaacggcc cggagggtgg 3900
cgggcaggac gcccgccata aactgccagg catcaaatta agcagaaggc catcctgacg 3960

```
gatggccttt ttgcgtttct acaaactctt ttgtttattt ttctaaatac attcaaatat   4020

gtatccgctc atgagactag gcttccgcgc cctcatccga aagggcgtat tcatatatgc   4080

ggtgtgaaat accgcacaga tgcgtaagga gaaaataccg catcaggcgc tcttccgctt   4140

cctcgctcac tgactcgctg cgctcggtcg ttcggctgcg gcgagcggta tcagctcact   4200

caaaggcggt aatacggtta tccacagaat caggggataa cgcaggaaag aacatgtgag   4260

caaaaggcca gcaaaaggcc aggaaccgta aaaaggccgc gttgctggcg tttttccata   4320

ggctccgccc ccctgacgag catcacaaaa atcgacgctc aagtcagagg tggcgaaacc   4380

cgacaggact ataaagatac caggcgtttc cccctggaag ctccctcgtg cgctctcctg   4440

ttccgaccct gccgcttacc ggatacctgt ccgcctttct cccttcggga agcgtggcgc   4500

tttctcatag ctcacgctgt aggtatctca gttcggtgta ggtcgttcgc tccaagctgg   4560

gctgtgtgca cgaacccccc gttcagcccg accgctgcgc cttatccggt aactatcgtc   4620

ttgagtccaa cccggtaaga cacgacttat cgccactggc agcagccact ggtaacagga   4680

ttagcagagc gaggtatgta ggcggtgcta cagagttctt gaagtggtgg cctaactacg   4740

gctacactag aaggacagta tttggtatct gcgctctgct gaagccagtt accttcggaa   4800

aaagagttgg tagctcttga tccggcaaac aaaccaccgc tggtagcggt ggtttttttg   4860

tttgcaagca gcagattacg cgcagaaaaa aaggatctca agaagatcct ttgatctttt   4920

ctacggggtc tgacgctcag tggaacgaaa actcacgtta agggattttg gtcatgagat   4980

tatcaaaaag gatcttcacc tagatccttt taaattaaaa atgaagtttt aaatcaatct   5040

aaagtatata tgagtaaact tggtctgaca gttagaaaaa ctcatcgagc atcaaatgaa   5100

actgcaattt attcatatca ggattatcaa taccatattt ttgaaaaagc cgtttctgta   5160

atgaaggaga aaactcaccg aggcagttcc ataggatggc aagatcctgg tatcggtctg   5220

cgattccgac tcgtccaaca tcaatacaac ctattaattt cccctcgtca aaaataaggt   5280

tatcaagtga gaaatcacca tgagtgacga ctgaatccgg tgagaatggc aaaagtttat   5340

gcatttcttt ccagacttgt tcaacaggcc agccattacg ctcgtcatca aaatcactcg   5400

catcaaccaa accgttattc attcgtgatt gcgcctgagc gagacgaaat acgcgatcgc   5460

tgttaaaagg acaattacaa acaggaatcg aatgcaaccg gcgcaggaac actgccagcg   5520

catcaacaat attttcacct gaatcaggat attcttctaa tacctggaat gctgttttcc   5580

cggggatcgc agtggtgagt aaccatgcat catcaggagt acggataaaa tgcttgatgg   5640

tcggaagagg cataaattcc gtcagccagt ttagtctgac catctcatct gtaacatcat   5700

tggcaacgct acctttgcca tgtttcagaa acaactctgg cgcatcgggc ttcccataca   5760

atcgatagat tgtcgcacct gattgcccga cattatcgcg agcccattta tacccatata   5820

aatcagcatc catgttggaa tttaatcgcg gcctagagca agacgtttcc cgttgaatat   5880

ggctcatact cttccttttt caatattatt gaagcattta tcagggttat tgtctcatga   5940

gcggatacat atttgaatgt atttagaaaa ataaacaaat aggggttccg cgcacatttc   6000

cccgaaaagt gccacctgac gtctaagaaa ccattattat catgacatta acctataaaa   6060

ataggcgtat cacgaggccc tttcgtct                                      6088
```

<210> SEQ ID NO 18
<211> LENGTH: 22
<212> TYPE: PRT
<213> ORGANISM: Erwinia
<220> FEATURE:

-continued

Figure 2:
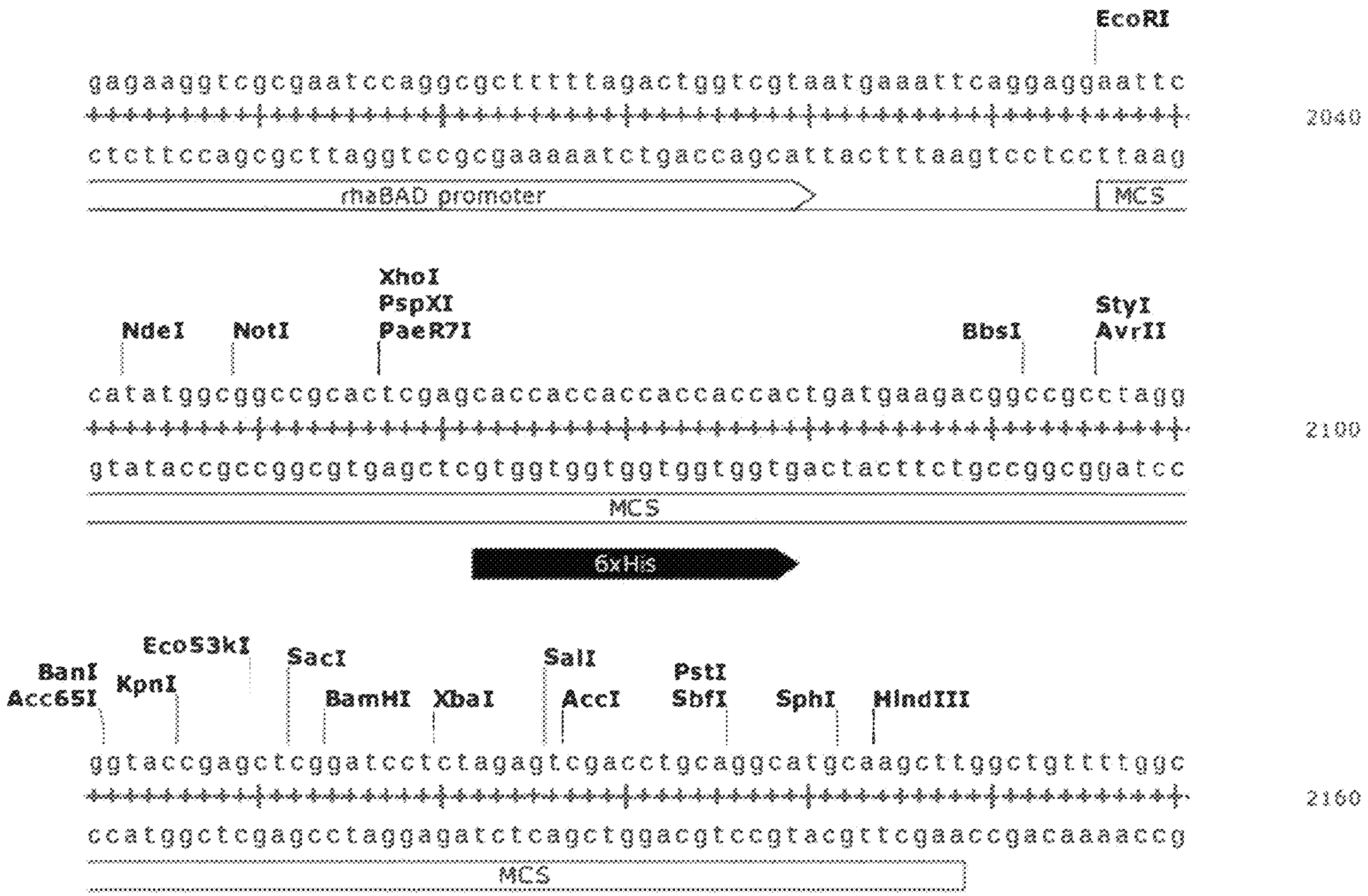
FIG. 2—The nucleotide sequence of the multiple cloning site (MCS) of KTXHIS (SEQ ID NO: 21)

```
<223> OTHER INFORMATION: PelB signal peptide - peptide

<400> SEQUENCE: 18

Met Lys Tyr Leu Leu Pro Thr Ala Ala Ala Gly Leu Leu Leu Leu Ala
1               5                   10                  15

Ala Gln Pro Ala Met Ala
            20


<210> SEQ ID NO 19
<211> LENGTH: 32
<212> TYPE: DNA
<213> ORGANISM: Artificial Sequence
<220> FEATURE:
<223> OTHER INFORMATION: SBamHI1680

<400> SEQUENCE: 19

gtacgctagg atcctgtggc agcaactgat tc                                  32


<210> SEQ ID NO 20
<211> LENGTH: 32
<212> TYPE: DNA
<213> ORGANISM: Artificial Sequence
<220> FEATURE:
<223> OTHER INFORMATION: BSalI1681

<400> SEQUENCE: 20

gtagataggt cgacagcgat cgtcattggg at                                  32


<210> SEQ ID NO 21
<211> LENGTH: 180
<212> TYPE: DNA
<213> ORGANISM: Artificial Sequence
<220> FEATURE:
<223> OTHER INFORMATION: Figure 2 - Multiple cloning site

<400> SEQUENCE: 21

gagaaggtcg cgaatccagg cgctttttag actggtcgta atgaaattca ggaggaattc     60

catatggcgg ccgcactcga gcaccaccac caccaccact gatgaagacg gccgcctagg    120

ggtaccgagc tcggatcctc tagagtcgac ctgcaggcat gcaagcttgg ctgttttggc    180
```